United States Patent
Moon et al.

(10) Patent No.: US 10,452,143 B2
(45) Date of Patent: Oct. 22, 2019

(54) APPARATUS AND METHOD OF IMPLANTABLE BIDIRECTIONAL WIRELESS NEURAL RECORDING AND STIMULATION

(71) Applicants: The San Diego University Research Foundation, San Diego, CA (US); Electronics Telecommunications Research Institute, Daejeon (KR)

(72) Inventors: Kee S. Moon, San Diego, CA (US); Yusuf Ozturk, San Diego, CA (US); Sung Q. Lee, Daejeon (KR); Woosub Youm, Daejeon (KR); Gunn Hwang, Daejeon (KR)

(73) Assignees: San Diego State University Research Foundation, San Diego, CA (US); Electronics and Telecommunication Research Institute (KR)

( * ) Notice: Subject to any disclaimer, the term of this patent is extended or adjusted under 35 U.S.C. 154(b) by 466 days.

(21) Appl. No.: 15/295,988

(22) Filed: Oct. 17, 2016

(65) Prior Publication Data
US 2017/0108926 A1 Apr. 20, 2017

Related U.S. Application Data

(60) Provisional application No. 62/244,162, filed on Oct. 20, 2015, provisional application No. 62/244,183, filed on Oct. 20, 2015.

(51) Int. Cl.
A61N 1/05 (2006.01)
G06F 3/01 (2006.01)
(Continued)

(52) U.S. Cl.
CPC ............ *G06F 3/015* (2013.01); *A61B 5/0031* (2013.01); *A61B 5/04001* (2013.01);
(Continued)

(58) Field of Classification Search
CPC ...... A61N 1/05; A61N 1/0529; A61N 1/0551; A61N 1/375; A61N 1/36103;
(Continued)

(56) References Cited

U.S. PATENT DOCUMENTS

2012/0134239 A1* 5/2012 Struthers ................ H04B 1/034
367/137
2015/0231397 A1* 8/2015 Nudo, Jr. ........... A61N 1/36103
607/62

(Continued)

*Primary Examiner* — Jon Eric C Morales
(74) *Attorney, Agent, or Firm* — Juneau & Mitchell; Todd Juneau

(57) ABSTRACT

A device and method is described for electronic human prosthetics, and specifically a skull- and/or spine implantable bi-directional neural-communication/brain-machine interface (BBMI) device where the input, output and on-board computing are combined into a single unit to form a compact neuro-prosthetics device. This invention is also directed to a fully implantable wireless spinal electronic recording and stimulation system using the BBMI in a human. The bi-directional devices (BBMIs) communicate with other bi-directional brain-machine interface devices (BBMI) and/or with external controllers wirelessly. The compact implantable stimulator has ultrasonic secondary battery charging system. One or more BBMI can be wirelessly connected so that a closed loop of BBMIs, or a BBMI and an external controller, can wirelessly send trigger pulses to this fully implanted stimulator over the spinal cord.

38 Claims, 28 Drawing Sheets

(51) Int. Cl.
*A61N 1/375* (2006.01)
*A61B 5/00* (2006.01)
*A61B 5/04* (2006.01)
*A61B 5/0478* (2006.01)
*A61B 5/048* (2006.01)
*A61N 1/36* (2006.01)

(52) U.S. Cl.
CPC ............ *A61B 5/048* (2013.01); *A61B 5/0478* (2013.01); *A61B 5/4064* (2013.01); *A61B 5/4836* (2013.01); *A61N 1/0529* (2013.01); *A61N 1/0551* (2013.01); *A61N 1/36103* (2013.01); *A61N 1/375* (2013.01); *A61B 5/0024* (2013.01); *A61B 2560/0219* (2013.01); *A61N 1/36082* (2013.01)

(58) Field of Classification Search
CPC ... A61N 1/36082; G06F 3/015; A61B 5/0031; A61B 5/0478; A61B 5/048; A61B 5/4064; A61B 5/4836; A61B 5/04001; A61B 5/0024; A61B 2560/0219
See application file for complete search history.

(56) References Cited

U.S. PATENT DOCUMENTS

2015/0380355 A1\* 12/2015 Rogers .................. H01L 23/538
257/773
2018/0085593 A1\* 3/2018 Fayram .................. H02J 50/20

\* cited by examiner

FIGURE 28

| | |
|---|---|
| Number of stimulation channels | 16 |
| Number of recording channels | 16 |
| Output characteristics | ±18V; 4-bank stimulation cluster |
| Waveform type | Bipolar phase |
| Pulse frequency | 0-250Hz |
| Pulse width | 100us-300us |
| Power dissipation | 25mW |

Where, V is input voltage, Cm, M, R is spring constant, mass, damping in mechanical system. Mr and Rr are acoustic parameters in media.

Where, $Gm$, $G0$ is the admittance, $R$ is impedance of transducer. $Rair$, $Rw$, $R0$ is the impedance of air, water and dc level, respectively.

APPARATUS AND METHOD OF IMPLANTABLE BIDIRECTIONAL WIRELESS NEURAL RECORDING AND STIMULATION

CROSS REFERENCE TO RELATED APPLICATIONS

This application claims priority to U.S. provisional 62244162 Apparatus and Method of Implantable Bidirectional Wireless Neural Recording and Stimulation, filed Oct. 20, 2015 and to U.S. provisional 62244183 Apparatus and Method for Wireless Controlled Implantable Spinal Stimulator, filed Oct. 20, 2015, the contents of both are incorporated herein in their entirety.

STATEMENT REGARDING FEDERALLY SPONSORED RESEARCH OR DEVELOPMENT

This invention was made with U.S. Government support under a contract with The National Science Foundation (NSF). The U.S. government has certain rights in the invention.

NAMES OF PARTIES TO A JOINT RESEARCH AGREEMENT

Not applicable.

REFERENCE TO A SEQUENCE LISTING

Not applicable.

BACKGROUND

Field of the Invention

This present invention is generally directed towards electronic human prosthetics, and specifically an implantable bi-directional neural-communication device where the input, output and on-board computing are combined into a single unit to form a compact neuro-prosthetics device.

Background of the Invention

Neuroplasticity is an intrinsic property of the human central nervous system (CNS) and represents the ability of actively adapting to environmental pressures, physiologic changes, and experiences. Neuroplasticity occurs either during normal brain development when people begin to process new sensory information, or as an adaptive mechanism to reform neurological paths due to brain or spinal cord injury (SCI). Damage to the CNS affects at least 2 million people per year. Compensation for brain or spinal function loss occurs after CNS injuries such as stroke or SCI. The result of this compensation may take place not only in the cortex, but also involves other subcortical parts. Thus, systems that can interpret different level of brain activity and use it to control mechanical and computer components have immense potential for applications in various fields.

Brain-computer-interfaces are systems that provide communications between human beings and machines. Brain-computer-interfaces can be used, for example, by individuals to control an external device such as a wheelchair. A major goal of brain-computer interfaces is to decode intent from the activity of an individual, and signals representing the decoded intent are then used in various ways to communicate with an external device. Brain-computer-interfaces hold particular promise for aiding people with severe motor impairments.

Electroencephalographic signals (EEG) acquired from scalp electrodes, and single neuron activity assessed by microelectrodes arrays or glass cone electrodes, are considered a safe and non-invasive modality, but have low spatial resolution, a poor signal to noise ratio due to signal attenuation by the skull, and signal contamination from muscle activity. In contrast, single-unit recordings of the signals from an individual neuron convey a significantly finer spatial resolution with higher information transfer rates and enable the use of more independent channels. However, single unit recordings require close proximity (within 100 microns) with neurons and therefore are not generally suitable for human applications because of the much higher associated clinical risk, and the lack of durable effect secondary to scar formation around the electrodes.

Devices implanted in or interfaced with the human nervous system today typically operate in open-loop mode and have yet to achieve the goals of processing neural data robustly, chronically, safely, and in a functionally meaningful way. For example, no implantable commercial pacemaker system exists today for fully closed-loop control system. Further, power supply remains an issue and rechargable batteries are not addressed within current integrated systems.

BRIEF SUMMARY OF THE INVENTION

In preferred embodiments, there are provided devices for, and methods of using, a bi-directional brain-machine interface (BBMI) device, comprising: (i) a biocompatible container housing an ultrasonic wireless power module, said power module comprises a piezoelectric composite transducer connected to a power rectifier circuit, and a rechargeable battery, wherein the piezoelectric composite transducer forms an internal part of a wireless two-part ultrasonic power transmission system having an external piezoelectric composite transducer paired with the internal part for wirelessly transferring power to recharge the rechargeable battery; (ii) a wireless radio frequency (RF) communication System on Chip (SoC) within the housing, said SoC having a processor core and powered by the power module, said processor core configured to control wireless data transmission and reception, said processor core configured to control charging of the rechargeable battery, said processor core configured to acquire sensor output data, said processor core configured to control stimulation input pulses, and said SoC configured to use low-power near field wireless communication; (iii) a sensor electronics module that interfaces with the SoC and comprises a digital electrophysiology interface chip, a programmable amplifier, and analog to digital converter, wherein the sensor electronics module is configured to record at least 16 channels of neural tissue activity; (iv) a stimulation module that interfaces with the SoC and comprises a pulse circuit configured to transmit electrical stimuli, wherein the pulse circuit is configured to generate at least 4 channels of stimulation; and, (v) a bidirectional microelectrode array that interfaces with the sensor electronics module and the stimulation module, wherein the bidirectional microelectrode array is configured to provide a bidirectional interface to record neural tissue activity and transmit electrical stimuli.

In another preferred embodiment, there is provided a BBMI device further comprising at least one spinal electrode connected to the stimulation module for transmitting electrical stimulation to the spine.

In another preferred embodiment, there is provided a BBMI device wherein the biocompatible container is a circular disc having a diameter ranging from 25-100 mm, and a height ranging from 8-30 mm, or wherein the biocompatible container is a circular disc having a diameter ranging from 28-75 mm, and a height ranging from 10-20 mm, or wherein the biocompatible container is a circular disc having a diameter ranging from 30-50 mm, and a height ranging from 10-20 mm, or wherein the biocompatible container is a circular disc having a diameter less than or equal to 35 mm, and a height less than or equal to 10 mm.

In another preferred embodiment, there is provided a BBMI device wherein the biocompatible container is comprised of one or more a materials selected from the group consisting of a metal, a polymer, or a composite.

In another preferred embodiment, there is provided a BBMI device wherein the biocompatible container is comprised of one or more a materials selected from the group consisting of titanium, Nitinol®, surgical steel, calcium, copper, zinc, iron, cobalt, magnesium, manganese, vanadium, molybdenum, silicate, strontium, tungsten, chromium, nickel, aluminum, and ceramics, composites, alloys, compounds, and mixtures thereof.

In another preferred embodiment, there is provided a BBMI device wherein the biocompatible container is comprised of one or more a materials selected from the group consisting of polyurethane (PU), polyesters, polyethers (PEEK), silicones, silicates, poly(vinyl chloride) (PVC), acrylates, methacylates, dextran, synthetic rubber (cis-polyisoprene), polyvinyl acetate, Bakelite, polychloroprene (neoprene), nylon, polystyrene, polyethylene, polypropylene, polyacrylonitrile, polyvinyl butyral (PVB), poly(vinylidene chloride), fluorinated polymers, polytetrafluoroethylene (PTFE), and mixtures and copolymers thereof.

In another preferred embodiment, there is provided a BBMI device wherein the biocompatible container comprises a biocompatible coating selected from calcium phosphate, tricalcium phosphate, or hydroxyapatite.

In another preferred embodiment, there is provided a BBMI device wherein the rechargeable battery is a Lithium ion battery.

In another preferred embodiment, there is provided a BBMI device wherein the processor core is configured to turn off module components that are not active to conserve battery.

In another preferred embodiment, there is provided a BBMI device wherein the low power near-field wireless communication comprises a 2.4 GHz protocol.

In another preferred embodiment, there is provided a BBMI device wherein the low power near-field wireless communication has a data rate ranging from 250 Kbps-2 Mbps.

In another preferred embodiment, there is provided a BBMI device wherein the low power near-field wireless communication comprises a Bluetooth Low Energy (BLE) communication protocol or an Enhanced ShockBurst (ESB) protocol.

In another preferred embodiment, there is provided a BBMI device wherein the low power near-field wireless communication has a transmit power ranging from 0.01-2.5 mW (−20 dBm to 4 dBm).

In another preferred embodiment, there is provided a BBMI device wherein the low power near-field wireless communication has a minimum data rate bandwidth of 1.5 Mbits/sec.

In another preferred embodiment, there is provided a BBMI device wherein the analog to digital converter is 16-bit.

In another preferred embodiment, there is provided a BBMI device wherein the sensor electronics module includes a built-in temperature sensor, and wherein the SoC is configured to monitor tissue temperature and implement device changes to avoid tissue damage from high temperatures.

In another preferred embodiment, there is provided a BBMI device wherein the sensor electronics module is configured to record at least 32 channels of neural tissue activity, or wherein the pulse circuit is configured to generate at least 16 channels of stimulation, or wherein the pulse circuit is configured to generate at least 32 channels of stimulation, or wherein the sensor electronics module is configured to record at least 32 channels of neural tissue activity and wherein the pulse circuit is configured to generate at least 32 channels of stimulation.

In another preferred embodiment, there is provided a BBMI device wherein the SoC is configured to monitor at least 32 channels of recorded neural tissue activity and wherein SoC is configured to direct the pulse circuit to generate stimulation to a pre-programmed channel of stimulation based on recorded neural tissue activity.

In another preferred embodiment, there is provided a BBMI device wherein the pulse circuit is configured to generate both single and bi-phase pulses.

In another preferred embodiment, there is provided a BBMI device wherein the SoC is configured to implement multiplexing of signals for stimulation and signals for recording.

In another preferred embodiment, there is provided a BBMI device wherein the SoC is configured to perform simultaneous power charging and wireless data transmission.

In another preferred embodiment, there is provided a BBMI device further comprising a memory device connected to the SoC, or further comprising a remote computer in wireless communication with the SoC.

In another preferred embodiment, there is provided an integrated bi-directional neural-communication and spinal stimulation system, comprising at least two of the BBMI devices, e.g. one for the brain and one for the spine, wherein the BBMI devices are configured to communicate and operate in a closed-loop, wherein a first BBMI device (brain) is configured to transmit a signal to a second BBMI device (spine) that is configured to receive the signal, and wherein the first BBMI device is configured to generate the signal when the SoC of the first BBMI device records neural tissue activity, and wherein the second BBMI device is configured to direct electrical stimuli when the SoC of the second BBMI receives the signal.

In another preferred embodiment, there is provided an integrated bi-directional neural-communication and spinal stimulation system that comprises three of the BBMI devices, e.g. brain-spine-forearm, wherein the BBMI devices are configured to communicate and operate in a closed-loop, wherein the BBMI devices are configured to transmit and receive signals to and from each other, wherein a first BBMI device (brain) is configured to generate the signal when the SoC of the first BBMI device records neural tissue activity, and wherein the second BBMI device (spine) is configured to direct spinal electrical stimuli when the SoC of the second BBMI receives the signal, and wherein the third BBMI device (forearm) is configured to generate a second signal when the SoC of the third BBMI device records peripheral neural tissue activity, and wherein the first BBMI device (brain) is configured to direct electrical stimuli when the SoC of the first BBMI receives the second signal (forearm).

In additional preferred embodiments, there are provided devices for, and methods of using, closed-loop, co-adaptive, bi-directional brain-computer interfaces (BBMIs) system, comprising: a biocompatible titanium container housing a piezoelectric composite transducer connected to a power rectifier circuit, and a rechargeable battery, wherein the piezoelectric composite transducer forms an internal part of a two part ultrasonic power transmission system having an external piezoelectric composite transducer paired with the internal part for transferring power to recharge the rechargeable battery; an RF module having a wireless transceiver, a circuit board, an antenna device, and a processor interface, said RF module connected to the rectifier circuit; said RF module comprising a multi-channel input/output bidirectional interface circuit connected to the wireless transceiver, said interface circuit configured to use low-power Bluetooth for near field wireless communication, wherein the interface circuit is configured to record 16 channels of neural tissue activity and the interface circuit is configured to generate 16 channels of stimulation; a microprocessor connected to the RF module, said microprocessor is used to control real time stimulation parameters such as frequency, duty-cycle, amplitude, etc. using periodic or continuous measurements of sensor signals, said microprocessor recording, controlling, and processing signal reception and transmission, said microprocessor connected to a memory device; and a sensor array connected to the RF module for receiving electric signals, and at least one electrode connected to the circuit component for transmitting electrical stimulation.

In another preferred embodiment, there is provided a method of transmitting a signal from a brain to a computer, comprising the steps: implanting the device of claim 1 into the skull of a patient with the sensor array and the electrode in operative communication with the brain of the patient; and, transmitting a signal from the device to an external receiver.

In another preferred embodiment, there is provided a method of treating a patient in need thereof, comprising the steps of: implanting the BBMI device in the skull of a patient in need thereof; and transmitting and receiving signals to and from the device to treat a disease or disorder selected from the group consisting of: epilepsy, motor command pathologies including paralysis, speech disorders, sleep apnea, pain, neurological tics, multiple sclerosis, neurological disorders, hearing or visual disorders, memory disorders, psychiatric disorders including depression, and cognitive disorders.

In another preferred embodiment, there is provided a method of treating a patient in need thereof, comprising the steps of: implanting the BBMI device in the skull of a patient in need thereof; and, transmitting and receiving signals to and from the device to enhance native processing of hearing, vision, speech, motor control, and other types of neuronal perception or control.

In preferred embodiments, there are provided devices for, and methods of using an implantable wireless spinal stimulator, comprising: a biocompatible titanium container housing a piezoelectric composite transducer connected to a power rectifier circuit, and a rechargeable battery, wherein the piezoelectric composite transducer forms an internal part of a two part ultrasonic power transmission system having an external piezoelectric composite transducer paired with the internal part for transferring power to recharge the rechargeable battery; an RF module having a wireless transceiver, a circuit board, an antenna device, and a processor interface, said RF module connected to the rectifier circuit; said RF module comprising a multi-channel input/output bidirectional interface circuit connected to the wireless transceiver, said interface circuit configured to use low-power Bluetooth for near field wireless communication, wherein the interface circuit is configured to record 16 channels of neural tissue activity and the interface circuit is configured to generate 16 channels of stimulation; a microprocessor connected to the RF module, said microprocessor is used to control real time stimulation parameters such as frequency, duty-cycle, amplitude, etc. using periodic or continuous measurements of sensor signals, said microprocessor recording, controlling, and processing signal reception and transmission, said microprocessor connected to a memory device; at least one spinal electrode connected to the RF module for transmitting electrical stimulation to the spine; and a sensor array connected to a brain-computer interface (BCI) on the the microprocessor for receiving electric signals from the brain.

In another preferred embodiment, there is provided a method of transmitting an electrical stimulus from a brain to a computer to a spine, comprising the steps: implanting the BBMI device into a lumbar area of a patient with the spinal electrode in communication with spinal nerve(s) and the sensor array in operative communication with the brain of the patient; and, transmitting a stimulus from the computer to the spine based on a signal from the brain to the computer.

In another preferred embodiment, there is provided a method of treating a patient in need thereof, comprising the steps of: implanting the BBMI device in the lumbar area of a patient in need thereof; transmitting and receiving signals to and from the device to treat a spinal disease or disorder.

In another preferred embodiment, there is provided a method of treating a patient in need thereof, comprising the steps of: implanting the BBMI device in the lumbar area of a patient in need thereof; and, transmitting and receiving signals to and from the device to enhance native processing of spinal nerve activity or control.

BRIEF DESCRIPTION OF THE DRAWINGS

FIG. 2(*b*) Top and bottom view of the system.

FIG. 2(*c*) System in the case in comparison with a quarter.

FIG. 10(*b*) Captured stimulation artifacts for 30 s.

FIG. 28 is chart showing details of the number of channels, and signal characteristics.

DETAILED DESCRIPTION OF THE INVENTION

Figure 1:
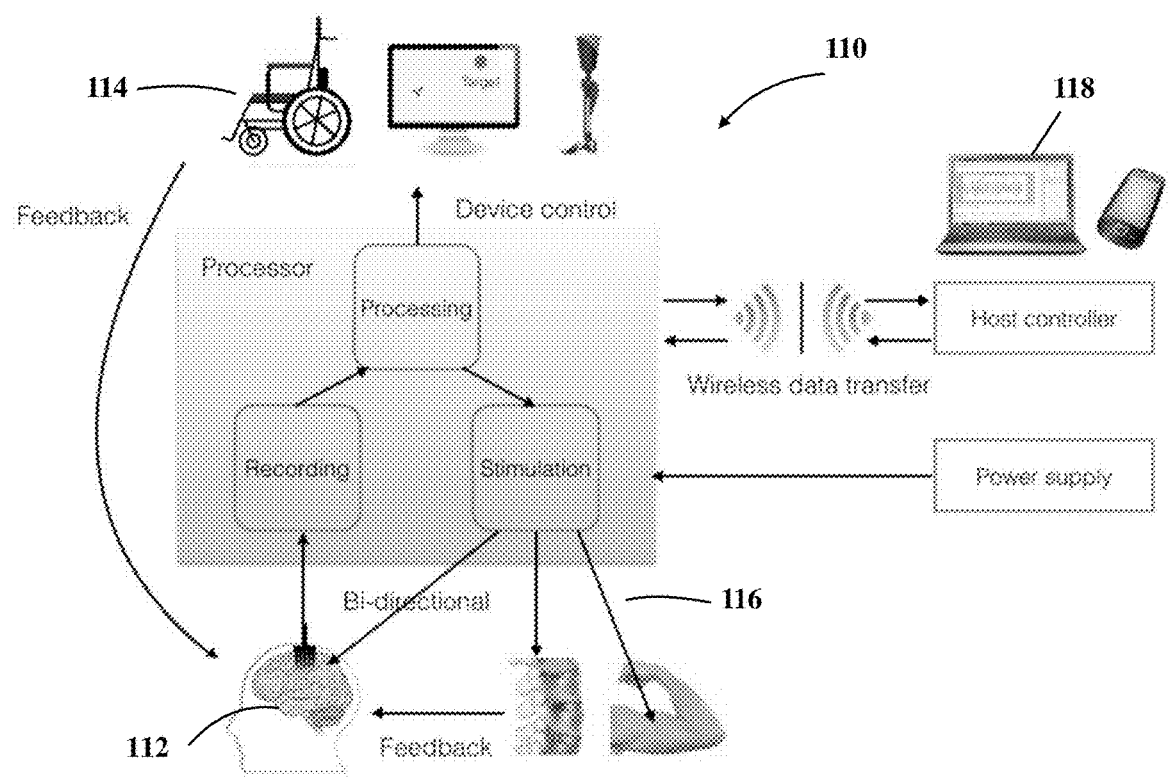
FIG. 1 is a diagram of a typical bidirectional BMI system structure.

The features, aspects and advantages of the present invention will become better understood with reference to the following description, examples, and claims.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Definitions

To facilitate understanding of the invention, certain terms as used herein are defined below as follows:

As used herein, the term "biocompatible" defines a two-way response, i.e. the body's response to the material and the materials response to the body's environment. The biocompatibility of a medical device refers to the ability of the device to perform its intended function, with the desired degree of incorporation in the host, without eliciting any undesirable local or systemic effects in that host. In preferred embodiments the biocompatible material of the invention is a medical grade or an implant grade material.

The term "closed loop" refers to a way in which we can accurately control a process by monitoring its output and "feeding" some of it back to compare the actual output with the desired output so as to reduce the error and if disturbed, bring the output of the system back to the original or desired response. The measure of the output is called the "feedback signal" and the type of control system which uses feedback signals to control itself is called a Close-loop System. A Closed-loop Control System, also known as a feedback control system is a control system which uses the concept of an open loop system as its forward path but has one or more feedback loops (hence its name) or paths between its output and its input. The reference to "feedback", simply means that some portion of the output is returned "back" to the input to form part of the systems excitation. Closed-loop systems are designed to automatically achieve and maintain the desired output condition by comparing it with the actual condition. It does this by generating an error signal which is the difference between the output and the reference input. In other words, a "closed-loop system" is a fully automatic control system in which its control action being dependent on the output in some way.

As used interchangeably herein, the terms "ECoG" and "electrocorticography" refer to the technique of recording the electrical activity of the cerebral cortex by means of electrodes placed directly on it, either under the dura mater (subdural) or over the dura mater (epidural) but beneath the skull.

As used interchangeably herein, the terms "bidirectional brain machine interface", "BBMI", "bidirectional brain-computer interface", "BCCI", and "neuro-computer interface", refer to a signal-processing circuit that takes input in the form of raw signals and converts the raw signals to a processed signal that can be input to a digital device for storage and further analysis.

A non-limiting example of BBMI is where a pair of implanted devices care used to wirelessly bypass damaged spinal neurons and allow the brain to communicate with intact spinal tissue below the injury site, such as in the examples below.

As used herein, the term "BBMI system" or "BCI system" refers to an organized scheme of multiple components including at least one BBMI as defined above, that together with secondary BBMI device(s), serve the function of translating raw signals to an output of a device, where the raw signals are derived from the central nervous system of a user of the system. The system may also optionally include a remote computer (non-implanted) that is used to record signals, send stimuli instructions, upgrade the software/firmware of the components, and so forth.

As used herein, the term "device" refers to a piece of equipment or a mechanism designed to serve a special purpose or function. In the examples, the device is a cursor on a video monitor. Other examples of devices within the intended meaning of the term include, without limitation, wheelchairs and prosthetics. The term also embraces mechanisms that can be used to control other mechanisms, such as steering wheels, joysticks, levers, buttons and the like.

As used herein, "low power" means less than 6 milliAmperes for transmitting and receiving, from a supply voltage of 2.0-3.5 V.

As used herein, "high data rate" means 200 kbps up to 1 Gbps, with data rates dependent on the particular modulation schemes used, the BER chosen, the SNR, and power consumption.

As used herein, "treatment" means reducing, eliminating, or ameliorating one or more signs or symptoms, temporarily or more permanently, during the treatment process or upon completion of the treatment process, of a disease, condition, or pathology generally recognized as a medical condition, diagnosis, complaint, or issue. "Treatment" may also include reduction of pain, allowing a patient to resume daily activities, reduction of pain medication, improved relaxation, physical therapy including therapy to improve strength, use, coordination, tone, blood supply and nerve conduction in and/or improved sleep.

Conditions contemplated as within the scope of the present invention include without limitation: chronic leg or arm pain, failed back surgery syndrome, complex regional pain syndrome, arachnoiditis, stump pain, angina, peripheral vascular disease, multiple sclerosis, spinal cord injury, stroke, non-stroke ischemic event, paralysis, brain injury, neurological pain, neurological injury of any kind, quadriplegic, paraplegic, traumatic brain injury, damage caused by cancer or arising from cancer treatment such as chemotherapy or radiation therapy nerves disorders, genetic or hereditary diseases, disorders or syndromes, epilepsy, neuralgia, tremor, Parkinson's, seizures, cervical or lumbar spinal disc or nerve disorders, neuropathic pain, sympathetically mediated chronic pain, and the like.

As used herein, the term "electrodes" refers to electrical components that deliver electrical charge to target tissue. Electrodes also include the leads that connect them to the pulse generators. Leads and electrodes must be durable as implants. Electrodes include epineural and cuff/encircling electrodes, as well as epimysial and intramuscular electrodes. Electrodes are preferably made from corrosion resistant materials such as platinum, iridium, stainless steel, or alloys. Eectrods may also include a Dacron backing to encourage ingrowth and permanence. Leads are commonly made from stainless steels, and alloys of Co, Cr, and Ni.

Referring to FIG. 1, Brain machine interfaces (BMI) provides a bidirectional communication link between brain and physical devices by offering an alternative path, bypassing the original pathway when it is no longer available. By decoding different patterns of brain activity into commands in real time, BMI can be used to control assistive devices, monitor the affective state of a patient during and after a rehabilitation session, and help the brain to regain motor functionality. The invention provides a new implantable wireless bidirectional brain machine interface (BBMI) for inducing cortical and spinal plasticity, creating new neural pathways.

In motor imagery based BMI systems, neural signals representing voluntary movement intentions are utilized to control physical devices. Neural signals recorded using invasive or to a limited degree non-invasive, sense electronics are processed for intention detection and the outcome can be used for controlling external devices.

The prior art either lacks the ability to integrate all functional components into a reasonably small size enclosure, or has a satisfactory size but is not fully bidirectional communication. The present invention provides a useful bandwidth, a high number of recording and stimulation channels, low power consumption, low noise, small size and functional processing features as part of the hardware and software of an implantable BMI solution.

The system developed is a multichannel, small form factor, low power and low noise solution for inducing activity dependent plasticity for neuro-rehabilitation and assessing brain response to stimulation. The system can provide 32-channel of brain activity recording from implanted electrodes and 4-channel of stimulation to brain or spinal cord based on a protocol submitted wirelessly to the device. The system utilizes a low power communication System on Chip (SoC) that can switch between Bluetooth Low Energy (BLE) and Enhanced ShockBurst (ESB) protocols for near field communication. Based on the brain activity report, the system allows one to induce stimulation to the brain and monitor brain response to that stimuli. The system utilizes ultrasonic power transfer for wirelessly charging an implanted secondary rechargeable battery. The hardware and component-based software platform that was developed was tested in vivo.

Bidirectional BMI System

Figure 2:
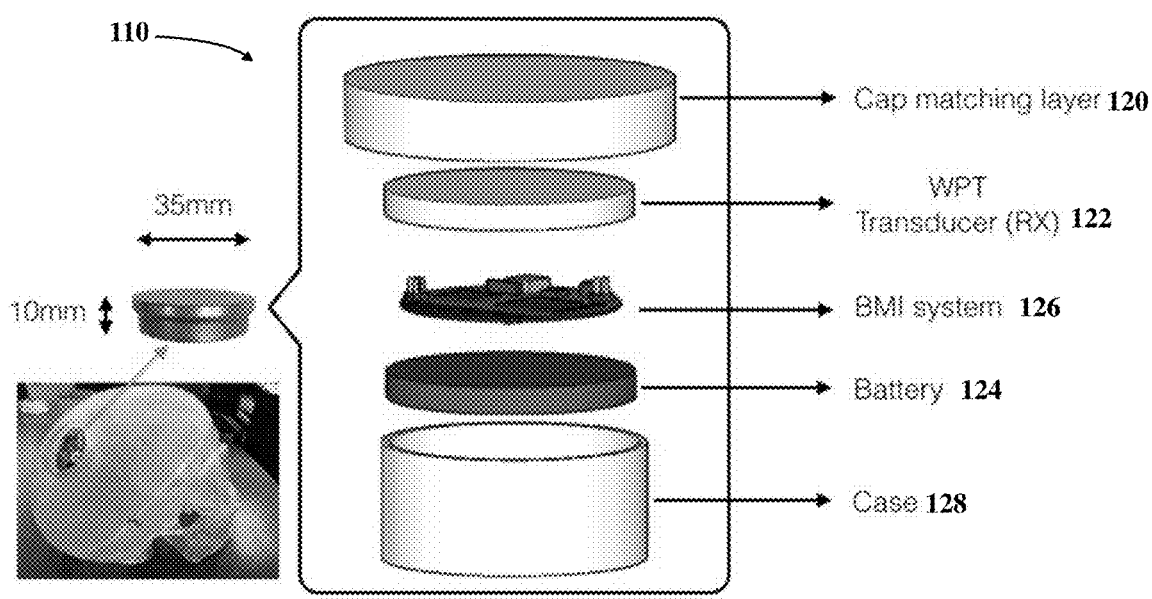
FIG. 2(*a*) System in titanium casing.
Figure 2:
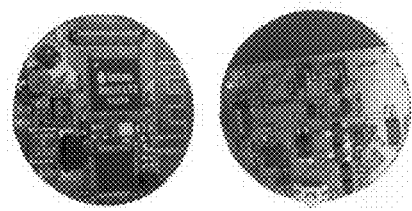
Figure 2:

The BBMI module developed in this study is encapsulated into a maximum 35 mm in diameter, 10 mm in thickness titanium casing as shown in FIGS. 2(a) and (c). Inside the casing, ultrasonic power transfer receiver is placed on top of the BMI module while the 3.7V Li-ion rechargeable battery is placed underneath.

In preferred embodiments, the BBMI device has a diameter ranging from 25-100 mm, and a height ranging from 8-30 mm, or a diameter ranging from 28-75 mm, and a height ranging from 10-20 mm, or a diameter ranging from 30-50 mm, and a height ranging from 10-20 mm, or a diameter less than or equal to 35 mm, and a height less than or equal to 10 mm.

In preferred embodiments, the biocompatible container is comprised of one or more a materials selected from the group consisting of a metal, a polymer, or a composite. Metallic materials include one or more a materials selected from the group consisting of titanium, Nitinol®, surgical steel, calcium, copper, zinc, iron, cobalt, magnesium, manganese, vanadium, molybdenum, silicate, strontium, tungsten, chromium, nickel, aluminum, and ceramics, composites, alloys, compounds, and mixtures thereof. Polymer materials include one or more a materials selected from the group consisting of polyurethane (PU), polyesters, polyethers (PEEK), silicones, silicates, poly(vinyl chloride) (PVC), acrylates, methacylates, dextran, synthetic rubber (cis-polyisoprene), polyvinyl acetate, Bakelite, polychloroprene (neoprene), nylon, polystyrene, polyethylene, polypropylene, polyacrylonitrile, polyvinyl butyral (PVB), poly (vinylidene chloride), fluorinated polymers, polytetrafluoroethylene (PTFE), and mixtures and copolymers thereof.

In another preferred embodiment, the biocompatible container comprises a biocompatible coating selected from calcium phosphate, tricalcium phosphate, or hydroxyapatite.

Invasive BMI refer to the method where sense electrodes are inserted into the brain (Intracortical electrode arrays) or sitting on the surface of the brain just beneath the skull (Cortical surface electrodes). In both cases the sense, communication and stimulation electronics may be placed under the skull, or may be designed to replace part of the skull as a skull implant, or may be placed between skull and skin or located completely outside the skull.

Figure 3:
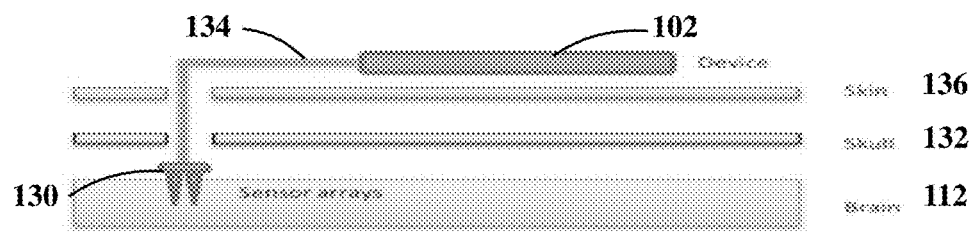
FIG. 3(*a*)-(*b*)-(*c*)-(*d*) four different invasive BMI system placement strategy.
Figure 3:
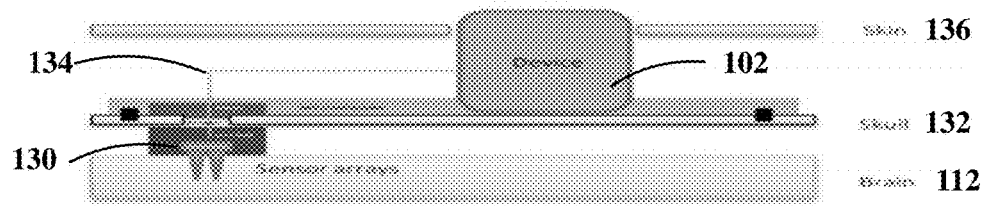
Figure 3:
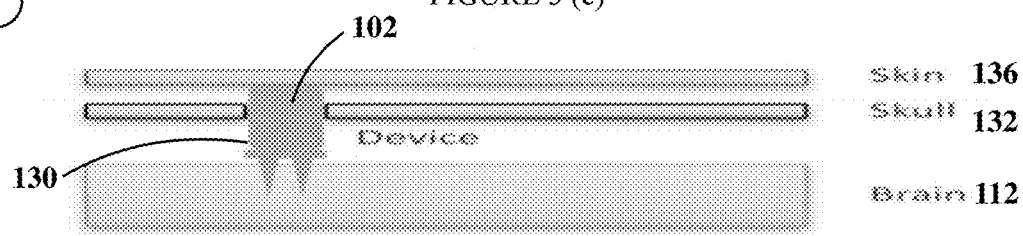
Figure 3:
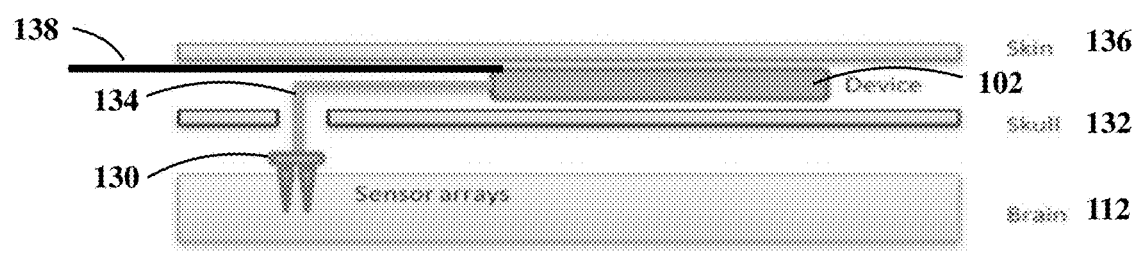

Referring now to FIG. 3, one placement is where only electrode arrays are implanted underneath the skull, data acquisition electronics are outside the body with wired connection between the two units as shown in FIG. 3(a). However, in a preferred embodiment, data acquisition electronics and battery module are enclosed in an aluminum housing, which is attached to the skull as shown in FIG. 3(b). The electrode as well as the data acquisition electronics are implanted through a small burr hole in the skull and secured to the skull as shown in FIG. 3(c). Implanted components can also be divided into two parts: sensor arrays and sealed recording electronics. Sensor arrays are implanted inside the skull while sealed recording electronics rests on the skull but underneath the scalp as illustrated in FIG. 3(d). This placement protects brain from direct thermal load, current leakage and contamination. The system with sensor array is placed inside a 50 mm craniotomy with the sensor side in direct contact with dura mater. Meanwhile, the antenna is placed between the skull and the scalp.

In a preferred embodiment of the present invention, a fully implantable BMI system is provided that can record from 32 channels and deliver 4 channels of stimulation. The system includes autonomous operation where the BMI records from the implanted electrodes, analyzes the signal and delivers stimulation where needed. The system also includes connected operation where the signal recorded is transmitted to a host processing system via a wireless communication channel and prescription updates are installed on the implanted module wirelessly. The entire system fits within a small titanium casing, which will be implanted as part of the skull as shown in FIG. 2(a) considering the risks for implants contamination. The system also includes a body area network that can collect inertial data and EMG from the subject in a free moving environment and aggregate the data in a host processing system wirelessly.

Figure 4:
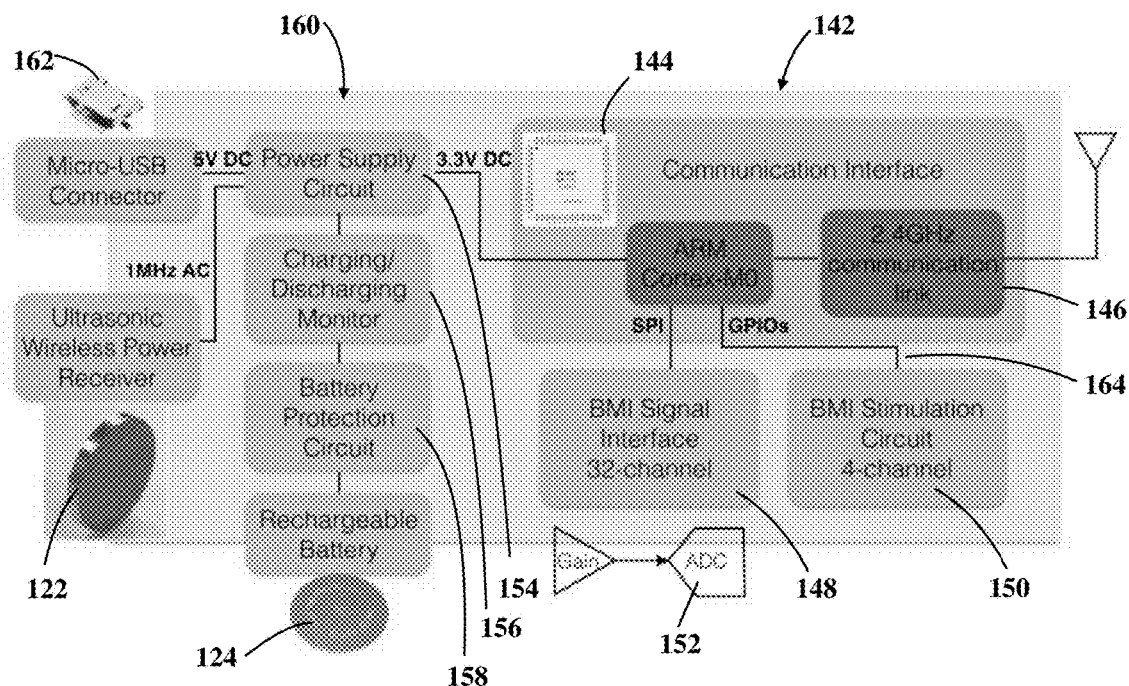
FIG. 4 Wireless BBMI system block diagram.

The detailed BBMI system block diagram is given in FIG. 4. The core component for the BMI system is a communication SoC with a Cortex-M0 processor core. The processor is employed for controlling 1) wireless data transmission. 2) charging current monitoring. 3) data acquisition and 4) stimulation configuration. Sense electronic module provides 32 input channels with a gain of 45.67 dB and small input referred noise. Stimulation module provides 4 output channels supporting unipolar 20V stimulus with programmable frequency and pulse duration. Power module consists of ultrasonic power receiver and the components for charge/discharge protection. Traditional USB charging is also available when ultrasonic power transfer is disabled. This component-based system with standard interfaces provides flexibility for integrating different modules together with minimum efforts. The PCB board is 30 mm in diameter while enclosed in the casing makes the diameter size 35 mm.

A. Sensors

Sensors are used for measuring the induced voltage when neurons are in active mode. For implantable BBMI devices, microelectrode arrays (MEA) are used as a bidirectional interface to sense extracellular neural activities and provide electrical signal input as stimuli. Among different types of MEAS, Utah Array is widely used for their excellent chronic stability. In this work, a Utah Array electrode (Blackrock Microsystems, Salt Lake City, Utah, USA) was implanted to the cortex of a primate prior to the experiment have been used for in vivo testing of the BBMI system presented. The impedance of the MEA implanted in the animal model is in the range of 0.5 MOhm to 2.5 MOhm.

B. Sensor Electronics Module

In order to acquire brain signals, RHD2132, a digital electrophysiology interface chips from Intan Technologies (Intan Technologies, Los Angeles, Calif., USA) has been used as an analog front end. This sense electronic module has a fully integrated electrophysiology amplifier array with on-chip 16-bit analog-to-digital converter (ADC) and industry-standard Serial Peripheral Interface (SPI). RHD2132 has a fixed gain of 45.67 dB (192) and a programmable range for amplifier bandwidth selection. Amplifier low cut-off frequency is in the range of 0.02 Hz to 1 kHz and high cut-off frequency is from 10 Hz to 20 kHz. The low and high cut-off frequencies are in a broad range that is capable of capturing different brain signals, which enables a wide range of recording from single unit recording Local Field Potential (LFP) to high frequency spike detection. The chipset is a complete low-power electrophysiological signal acquisition system specifically designed for dedicated brain signal recording system. With a built in temperature sensor, even small temperature changes can be monitored to avoid thermal issues generated by the system to damage the surrounding tissues.

C. Wireless Communication Module

Figure 5:
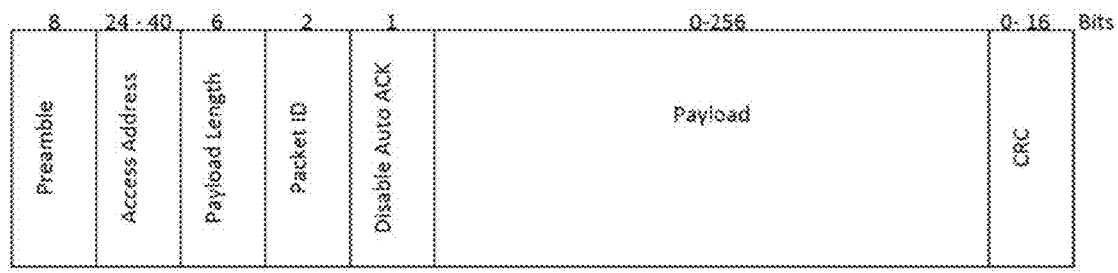
FIG. 5 ESB protocol packet structure.

A low energy communication SoC by Semiconductor (nRF51822, Nordic Semiconductor, Oslo, Norway) provides the wireless interface between the sense electronics module and any host that can integrate 2.4 GHz protocol stacks. The nRF51822 communication SoC supports three data rates 2 Mbps, 1 Mbps and 250 kbps. Depends on different targeting signals extracted from the brain, transmission of raw brain data requires a high throughput. In case of LFP, approximately 700 Kbps for the transmission of 32 channels with sampling rate lk samples per second (SPS) on 16 bits resolution. A proprietary Enhanced ShockBurst (ESB) protocol is used for communicating brain signals to a host computer. ESB protocol has a dynamic payload length from 1 to 32 bytes and minimal connection interval can be set to 1.2 ms. FIG. 5 shows the packet structure of the ESB protocol.

The preamble: The nRF51822 has a preamble comprised of alternating sequence of 0s and 1s. In the packet, 8 bits are allocated for the preamble before access address bits.

The access address: The on-air addresses that consist of base address and prefix address are 3-5 bytes.

Prefix address: Each logical address on the nodes is called a pipe and each of the 8 pipes has a unique byte-long prefix address.

Base address: ESB protocol provides three length options for base addresses: 2 bytes, 3 bytes or 4 bytes. Moreover, two different base addresses are used in ESB protocol to identify pipes. The base address 0 is for pipe 0, and the base address 1 is for the rest of the pipes.

Packet Control Field: 9 bits are allocated for signal length, identification, and acknowledgment. 6 bits are employed to indicate payload length. 2 bits are used for packet identification to distinguish a new packet from a former packet. The ESB protocol supports both transmit with acknowledgment and transmit without acknowledgment mode. With 1 bit indication, auto-acknowledgment can be disabled. Therefore, Primary Receiver (PRX) does not respond with any acknowledgment after the packet has been received from Primary Transmitter (PTX). Otherwise, PTX requests acknowledgment message from the receiver side noticing a transmission as successful.

Payload: The objective part of a packet to transmit is a payload that dynamically range from 0 to 32 bytes. PTX contains payloads with actual data that need to be sent to the host and PRX contains the acknowledgement data.

Cyclic Redundancy Check (CRC): ESB protocol has an option to use CRC, which is an error-detecting code to recognize changes in the raw data. Based on user demand, CRC check can be set to 8-bit, 16-bit or disabled.

On the receiver side, a dongle with an nRF51822 chip and a USB controller are integrated to receive data over the wireless link. If the packet is sent for the first time from transmitter, and the RX-FIFO on the receiver has free space for the packet, the packet will be put on the RX-FIFO, then acknowledgment will be sent to the transmitter. The received data will pass to the host processor through serial interface.

The overall component-based architecture provides a system level flexibility to integrate different sensors into one sensor network. Also contemplated in a preferred embodiment is a body area network node with an integrated EMG sensor and a 9-axis inertial sensor. The body area network node can readily be integrated with the electrophysiological interface presented in this study which extends the sensorimotor feedback capabilities of the system. The body area network can host 7 such network nodes deployed on the same person.

D. Stimulation module

Intracortical Microstimulation (ICMS) is a stimulation method that delivers relatively low but high frequency current pulse to sensor arrays implanted under the skull. ICMS is used in research on neuroprosthetics as a feedback input delivered to sensory areas. Direct intracortical stimulation is applied to a BMI system for enacting arm-reaching movement.

Applying stimulation to brain or spinal cord is used for treatment of certain conditions that affect CNS. The system according to the present invention supports 4-channel high voltage stimulation for cortical stimulation or spinal cord stimulation. Stimulation voltage is set to 20V with a minimum pulse width of 1 microsecond. The stimulation frequency can be as high as 250 stimulation pulses per second. Considering 0.5 MOhm to 2.5 MOhm electrode impedance, stimulation current is in the range of 8 uA to 40 uA. Stimulation with different parameters for different purposes can be issued while brain activities can be recorded at the same time. Based on the brain activity report, the system is used to induce stimulation and monitor brain response to stimulation.

Wireless Power Transfer and Power Budget

Traditionally single-use, non-rechargeable batteries, such as those used to support pulse generation in cardiac pacemakers and deep brain stimulators, usually have a predetermined lifetime which will result in frequent surgeries to have the battery replaced.

For the implantable BMI system with components close to vital organs, rechargeable batteries that can be powered and recharged wirelessly are considered as a more viable option and include radio frequency (RF), ultrasound, infrared light, low-frequency magnetic field charging. Other non-conventional energy harvesting solutions such as charging battery using energy produced by physiological environment or body movements are also contemplated as within the scope of the present inventive subject matter.

Figure 6:
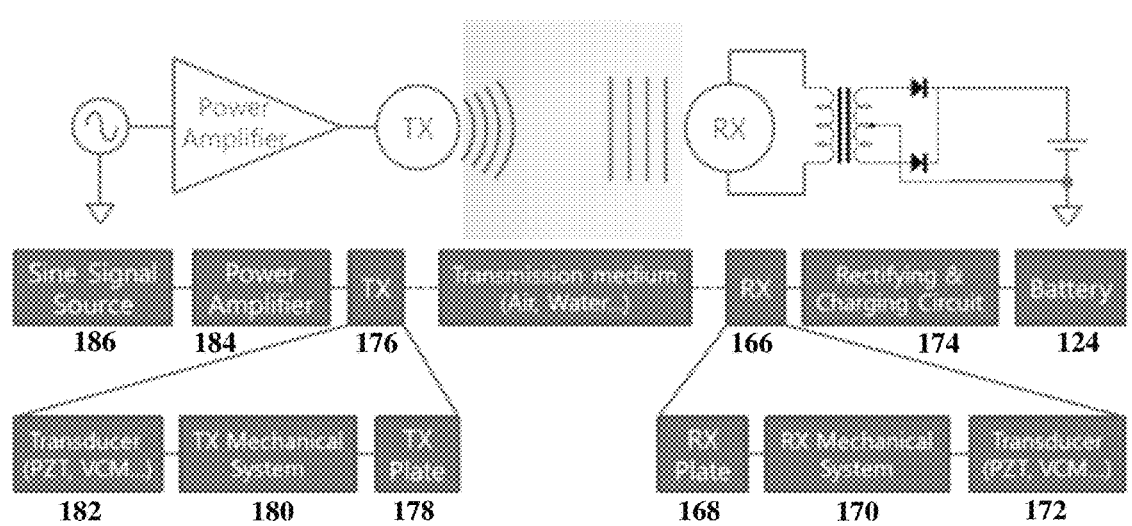
FIG. 6 Block diagram of wireless power transfer system using ultrasonic resonance.

As illustrated in FIG. 6, ultrasonic wireless power transmission is composed of converting electrical energy and ultrasonic energy to each other. In order to deliver enough power to the system, ultrasound must be conveyed with high efficiency. To achieve high efficiency of the ultrasound propagation in the skin, the spherical spreading and attenuation of the sound wave should be considered. The energy transmission efficiency is based on many factors. In order to achieve the best efficiency during power charging period, factors such as frequency and amplitude need to be tuned accordingly. By using ultrasonic cavitation gel between Transmitter (TX) and Receiver (RX) to act like the human skin, the best efficiency achieved is about 18% to 20%.

The sensor module is designed to operate using a coin type rechargeable battery with a 30 mm diameter. To extend the lifetime of the system between charges, an elegant power management scheme is employed to turn off module components when they are not active to conserve battery. Transmit power is one of the radio characteristic that affects power consumption in wireless communication systems. ESB protocol supports radio solution with transmit power ranging from −20 dBm to 4 dBm. A 6.22% increase in power consumption is observed when transmit power change from −20 dBm to 0 dBm.

Sampling rate is another factor that influence the power consumption. The total power consumption of the data acquisition module depends on different configurations. A comparison given in Table 1 highlight the relationship of power consumption and sampling rate for 1 kSPS and 30 kSPS. There is an increase of 212% in power consumption when the sampling rate is increased from 1 kSPS to 30 kSPS.

TABLE I

ENERGY BUDGET FOR IMPLANTABLE BBMI

| Components | 1 kSPS | 30 kSPS |
|---|---|---|
| Baseline amplifier array current | 200 μA | 200 μA |
| Amplifiers | 16 * 7.6 μA/kHz * 1 kHz = 122 μA | 16 * 7.6 μA/kHz * 10 kHz = 1220 μA |
| Baseline ADC current | 510 μA | 510 μA |
| ADC/MUX | 2.14 μA(kSPS) * 19 * 1 kSPS = 40.7 μA | 2.14 μA(kSPS) * 19 * 30 kSPS = 1219 μA |
| Temperature sensor | 70 μA | 70 μA |
| Total current consumption | 1.03 mA | 3.22 mA |
| Total power consumption | 3.4 mW | 10.62 mW |

Figure 7:
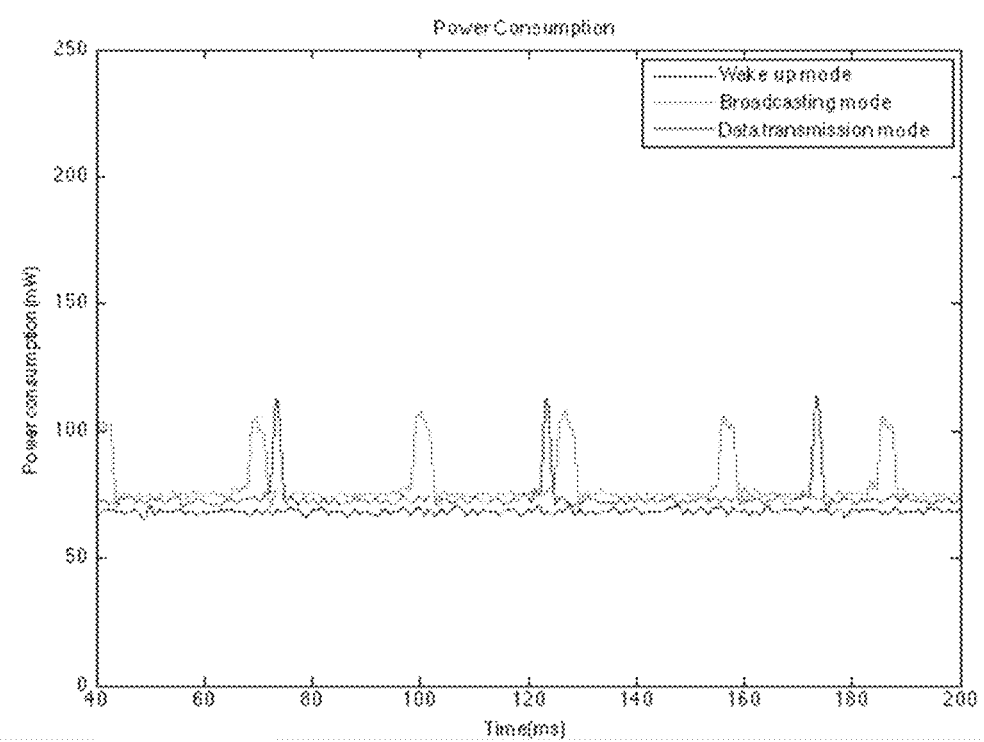
FIG. 7 Power consumption for different configuration mode.

FIG. 7 shows an examination of power consumption with a given configuration, and specifically the energy consumed during each one of the following states based on communication protocol state: device wake up, advertising and data transmission. In FIG. 7, blue plot represent the power consumption during device wake up. Green plot represent the power consumption in advertising mode and red plot shows power consumption in data transmission mode. The mean power consumption in device wake up mode is about 68.54 mW while the mean power usage in broadcasting mode is approximately 78.25 mW. The power consumption during data transmission is measured about 74.05 mW. The power consumption is calculated with a resistor value 5.920 hm and supply voltage of 3.71V. The current consumption is in the range of 18.47 mA to 19.96 mA when device is in normal operation status.

The sensor is powered by one Li-Ion rechargeable battery, which has a nominal capacity of 200 mAh and a nominal voltage of 3.7V. As a result, it can provide about 10 hours of working time without recharging the battery.

Recording and Stimulation

Figure 8:
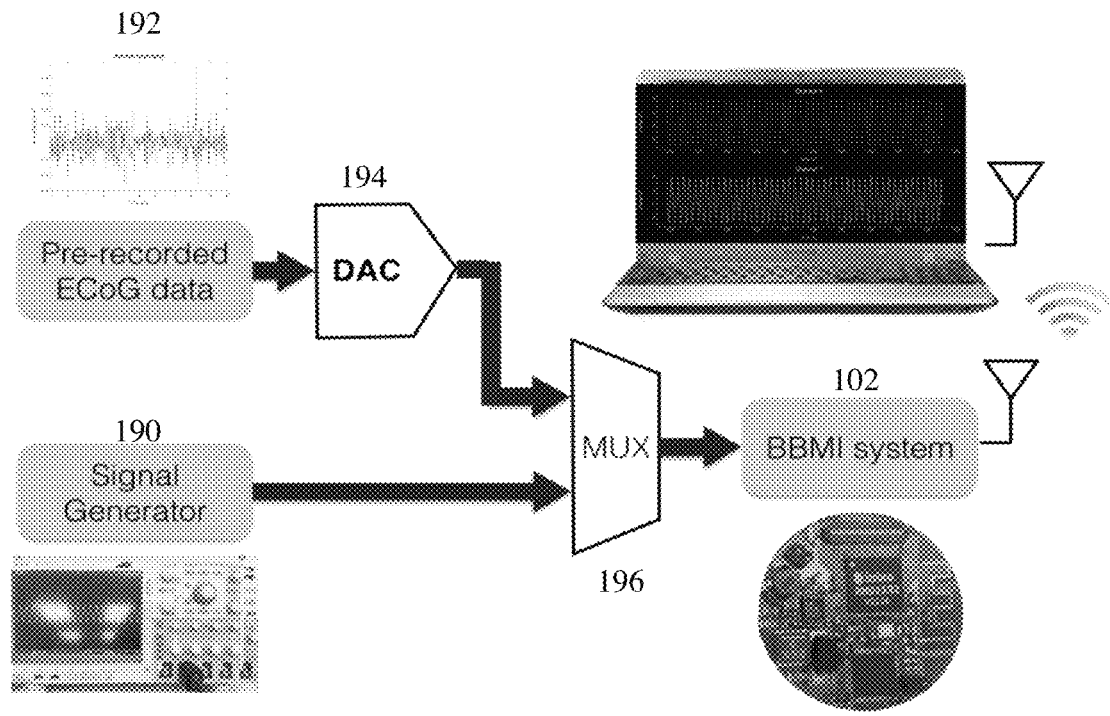
FIG. 8 Experimental setup for bench test.

Referring now to FIG. 8, the system is able to transmit data in three different transmission rates. For the bench test, we set on air data rate to be 1 Mbps. On the receiver side, baud rate is set to 1 Mbps. Sampling rate was set to be 800 SPS for one channel. With 16-channel enabled, we were able to achieve 800 SPS data rate with ESB protocol. A user interface is designed with Python to read and plot data through serial port.

As shown in FIG. 8, two different input sources are fed into the BBMI device 102 for bench test. The input signal range for this device is ±5 mV. One test source, Signal Generator 190, generates a sine wave with amplitude 3.3 mV, frequency change dynamically from 1 Hz to 100 Hz. Another test source, Recorded Intracortical Signal 192, is a set of pre-recorded intracortical signal recorded from an animal model using a research grade recording system. The intracortical data stream was first fed into a Digital-Analog Converter (DAC) 194 and then to the input multiplexer 196 of the BBMI device 102. All data received in the host side were plotted in real-time and saved to a .csv file locally for validation. Stimulation module was validated by using scope to monitor the output stimulus amplitude and frequency.

Certain frequency bands have been identified with certain types of cortical activation. Alpha rhythms (over visual cortex) and mu rhythms (over somatosensory cortex) are 8-12 Hz and are thought to be the product of thalamocortical circuits which show suppressed frequency power on cortical activation. These power suppressions are also known as Event Related Desynchronizations (ERD). The mu rhythms can also often associated with beta rhythms (18-26 Hz) but are separable in regards to timing and topographical distribution. More regionally specific higher frequency bands, known as gamma rhythms (>30 Hz), have also been investigated. The gamma band is often associated with an increased power (Event Related Synchronization—ERS) in association with cortical activation and has been postulated to be associated with motor programming, attention, and sensorimotor/multimodal sensory integration.

EEG has been the most commonly used technique for acquiring these electrical signals of activity because EEG is non-invasive and therefore low risk, is relatively low-cost, and is widely applicable. However, due to signal attenuation by the skull and electrical noise contamination from muscle activity, the signal-to-noise ratio of EEG is low and the spatial and frequency resolution is poor. The maximal spatial discrimination with EEG is approximately 3 centimeters and the appreciable frequency range is 0-40 Hz. Magnetoencephalography is also a non-invasive modality with a similar profile as that of EEG, but has an improved spatial resolution of approximately 4 to 10 millimeters. In contrast, ECoG requires a craniotomy for electrode placement. Though invasive, the ECoG platform provides a combination of high spatial resolution on the order of 1-2 mm with a broader frequency range of approximately 0-200 Hz.

Conventional (i.e., EEG-based) BCI systems use very specific signals in limited frequency ranges below 40 Hz. Examples of such signals include the mu/beta rhythms (around 10/20 Hz, respectively), slow cortical potentials, and P300 evoked potentials. In contrast, since ECoG signals have a much higher frequency range, and higher spatial resolution, ECoG signals exhibit different signal characteristics. Accordingly, electrode locations or frequencies that are used in conventional EEG-based systems are not helpful in ECoG-based systems. Until now, the electrode configurations, frequencies and signal characteristics useful in ECoG-based systems though investigated have never been used and defined for online control. The present ECoG-based BCI system uses a distinct set of signal characteristics and analyses.

Use of electrocorticography signals in a BBMI system enable an individual to maintain continuous device control in real time and with continuous feedback using electrocorticographic signals. The ECoG signal is recorded from electrodes positioned at the skull surface, with lower clinical risks than intra-cortical electrode devices, while at the same time offering a much more robust signal than EEG, both in terms of spatial and resolution and temporal resolution. The ECoG signal magnitude is typically five to ten times larger (0.05-1.0 mV versus 0.01-0.02 mV for EEG) than EEG, has a much higher spatial resolution as it relates to electrode spacing (0.125 cm versus 3.0 cm for EEG), and has more than four times the frequency bandwidth of EEG (0-200 Hz versus 0-40 Hz for EEG). Thus, ECoG signals represent a smaller population of neurons than does EEG, and discriminate across a broader range of frequencies including frequencies greater than 40 Hz. An ECoG-based BCI not only enables the full use of mu rhythms, but also the use of the much higher frequency bands (beta and gamma) that are thought to be more closely associated with higher specific cortical function.

In a preferred embodiment, the invention contemplates the use of both subdural electrodes and intra-cortical microelectrodes.

In another preferred embodiment, the signal is routed through a network. In another embodiment, the signal is routed to a user feedback screen. Raw and processed signals from the acquisition device, and the device command, can be communicated via a local area network to one or more computers. As with other electronic devices, the signal may be further passed through a low pass-filter, amplifiers, oscillators, modulation devices, encoding devices, and A-D/D-A converters.

More preferably, the invention provides a new implantable bi-directional neural-communication device where the input, output and on-board computing are combined into a single unit to form a compact neuro-prosthetics device.

Since the BBMI device has a small form factor, the method of implantation does not require the complexity of complicated multi-component device having external hardware requirements. A craniotomy involves making a incision to remove the overlayer of skin and access the skull. A portion of the skull is removed to create a cavity larger enough to accommodate a BBMI device. Depending on the treatment, any region of the skull can be used, including parietal, temporal, frontotemporal, and occipital. In one embodiment, the BBMI device does not require any further leads or electrodes to be attached and the BBMI device may be cemented in place, and the surgical wound closed. In another embodiment, the BBMI device is connected to electrodes or electrode arrays that are positioned and the BBMI device tested to make certain of a good connection. Once the BBMI device is shown to be transmitting and receiving signals, receiving power from the ultrasonic source, and able to provide electronic stimuli pulses, the surgical wound is closed.

The BMMI device and method of implantation provides the advantages over the conventional implantation of devices. Provides structural soundness, ease of battery charging for the implant, charging efficiency, and better wireless communication that meets a particular systems signal to noise ratio and bit error rate. Further, the invention provides an advantage of easy replacement, better quality of life for patients, and less visible scarring.

The interface device can be can be connected using existing networking technologies such as Bluetooth for wireless data communication. The on-board computation circuit provides intelligent data prioritization to handle the varying nature of emergencies and notifies the healthcare provider automatically using the wireless network. The on-board computation circuit supports remote configuration programming input to allow the system to be modified/updated by the healthcare provider (see e.g. FIG. 1). The interface device has an integrated ultrasonic power transfer through the skin for wirelessly charging an implanted secondary rechargeable battery that provides several advantages over the conventional wireless recharging technologies including the small form-factor, low-temperature effect, deep power transmission distance, etc. The implantable bi-directional neural-communication device will use a custom portable recharging system using ultrasonic power transmission. The device will provide a fully closed-loop system for automatically controlled neural prosthetics for various implantable medical applications.

B. In Vivo Test

Brain recordings can be broadly classified into two categories. The signals below 300 Hz are called LFPs and relates to increased brain activity in a particular area while signals above 1000 Hz provide more detailed information on neural spikes. To record neural spikes the sampling rate should be set to 15 kSPS and above while for LFPs sampling rates around 2 kSPS is adequate. Using intracortical electrode arrays, single unit activity (SUA), multiple unit activity (MUA) and LFP can be recorded while cortical surface electrodes enables recording LFP and Electrocorticography (ECoG) from the surface of the brain. LFP records and samples the field electrical potential from a small group of neurons. It records sensorimotor rhythms similar to ECoG but with higher spatial resolution. Further, in order to analyze integrative synaptic processes, LFP is the signal of interest instead of spikes because synaptic processes cannot be captured by spike activity of a small number of neurons.

LFP is used to study higher-level cognitive processes involving attention, memory and perception, as well as to control prosthetic devices. LFP is used for monitoring neural activity in human recordings since the signal can be captured more easily and stably in chronic settings contrary to spikes. Thus, in vivo tests of the system were performed on a behaving monkey to record his LFP oscillations. The animal model employed in the study has Utah array implanted in cortical areas to observe LFP oscillation that related to hand motion. The Utah array is connected to external recording and stimulation units via a connector installed on the skull. The front end amplifier lower bandwidth is set to 0.1 Hz and higher bandwidth is set to 1 kHz. An on board high-pass filter is enabled with a cutoff frequency of 0.3 Hz.

Figure 9:
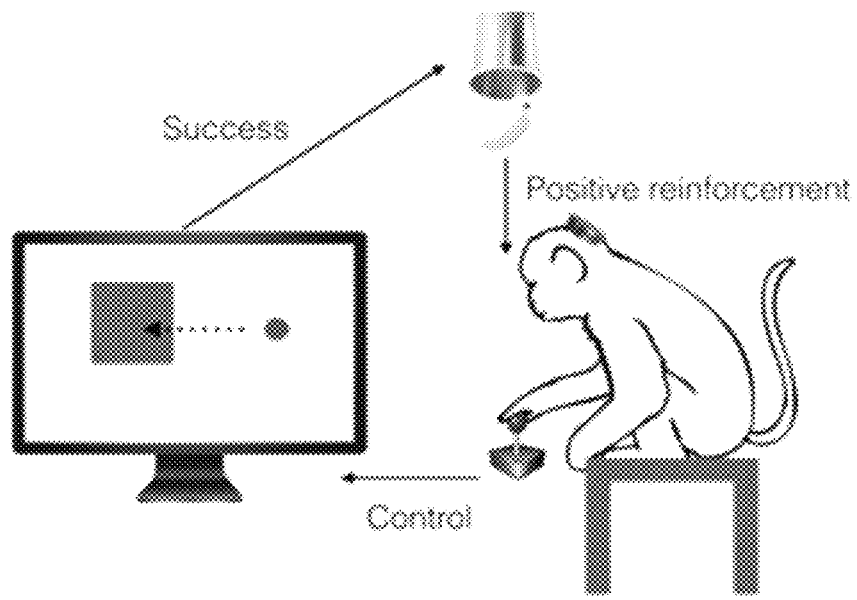
FIG. 9 Experimental setup for in vivo test.

Referring now to FIG. 9, an experimental setup for obtaining in vivo signal results is illustrated. A monkey was positioned securely in front of a PC monitor playing a game. A specific visual cue was presented in the monitor, in this case, a rectangular box will pop up randomly in screen. The monkey had to move the cursor in the screen towards the rectangular box by controlling a joystick. If the monkey successfully moved the cursor into the rectangular area, the monkey was rewarded by giving treats.

Figure 10:
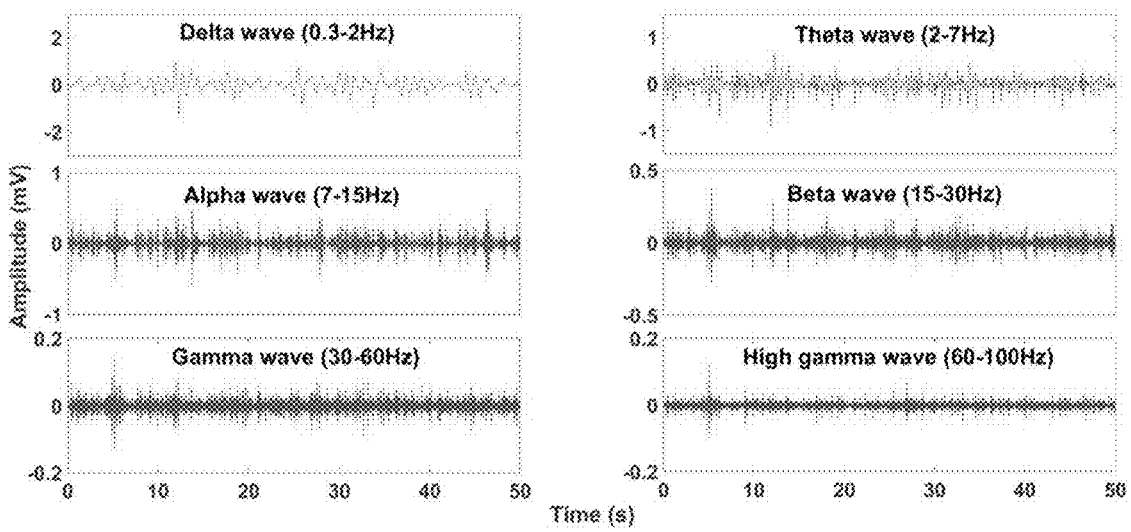
FIG. 10(*a*) Different brain rhythms of the LFP recorded from Monkey's motor cortex.
Figure 10:
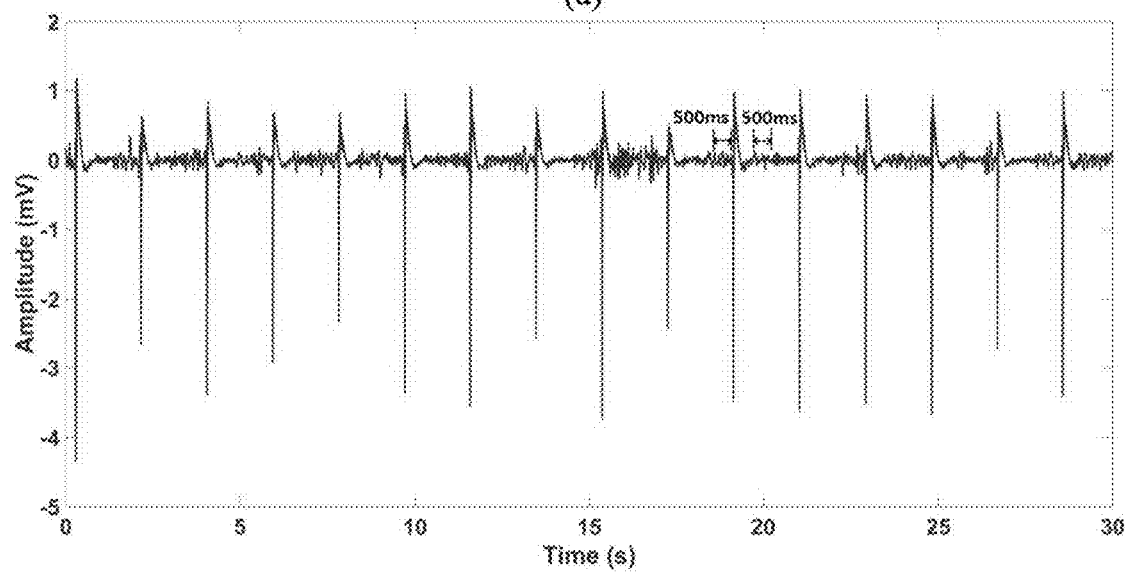

Referring now to FIG. 10(a), during the experiment, normal LFP was first recorded for 1000 seconds, signals are band-passed into different rhythms as shown. Six band pass filters are applied to the data stream. They are: delta wave (0.3 Hz-2 Hz), theta wave (2 Hz-7 Hz), alpha wave (7 Hz-15 Hz), beta wave (15 Hz-30 Hz), gamma wave (30 Hz-60 Hz) and high gamma wave (60 Hz-100 Hz).

In the next part of the experiment, stimulation module was tested by issuing a stimulation pulses with a current rating between 8 µA and 40 µA. Stimulus period was set to 1.6 seconds. Stimulation artifacts can be observed from the recording data as shown in FIG. 10(b).

Figure 11:
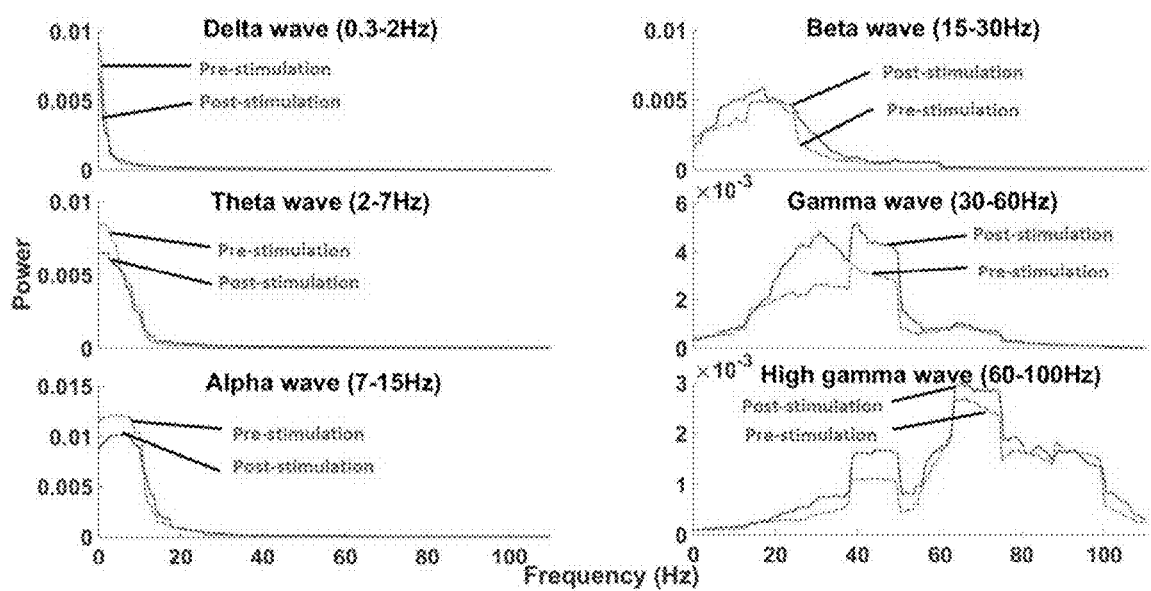
FIG. 11 Pre-stimulation and post-stimulation frequency domain power comparison for one single stimulus.

Referring now to FIG. 11, the frequency domain signals in 6 different frequency bands for both pre-stimulation and post-stimulation period for a single stimuli are shown. The signals 100 ms ahead of issued stimuli and 100 ms after issued stimuli were compared. The blue line represents pre-stimulation and the red line shows post-stimulation. FIG. 11 shows an energy increase in higher frequency band beta, gamma and high gamma. But no energy changes for low frequency band delta and theta. After the stimulations were issued periodically for 1000 seconds, normal LFP was recorded again.

Figure 12:
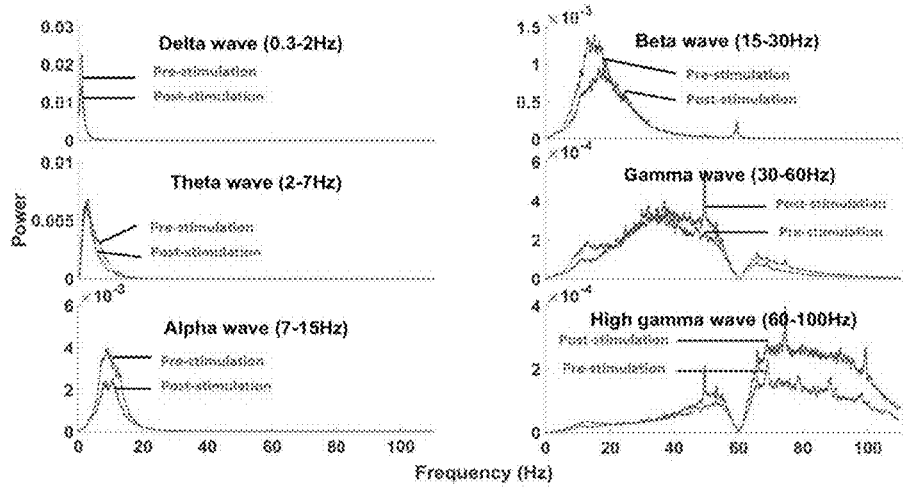
FIG. 12(*a*)-(*b*)-(*c*)-(*d*) Pre-stimulation and post-stimulation power comparison for each frequency band recorded from 4 different locations.
Figure 12:
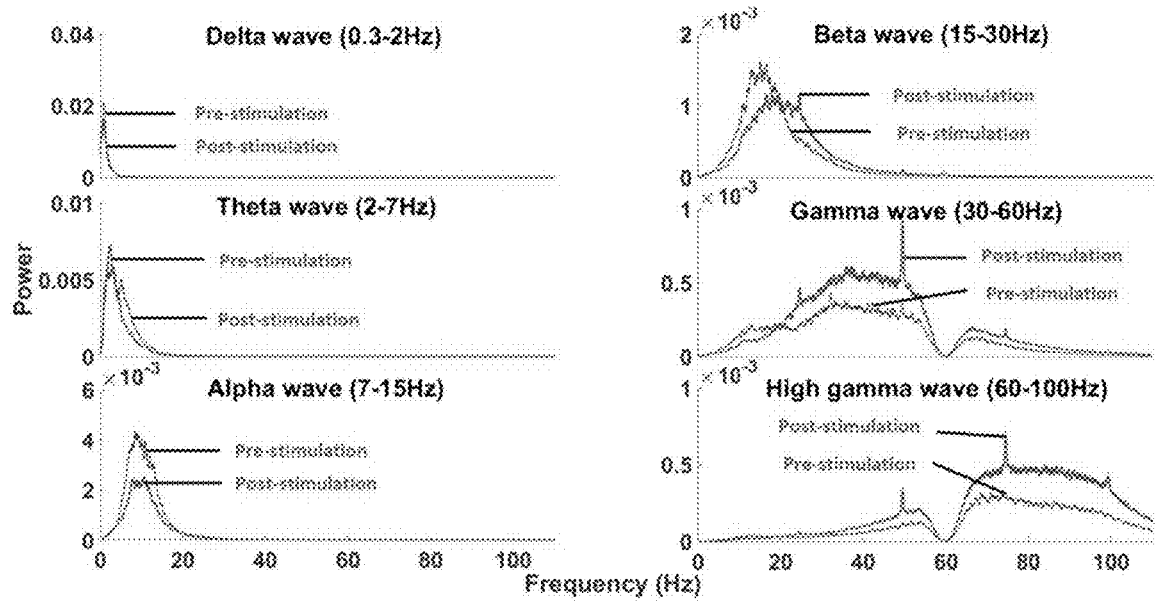
Figure 12C:
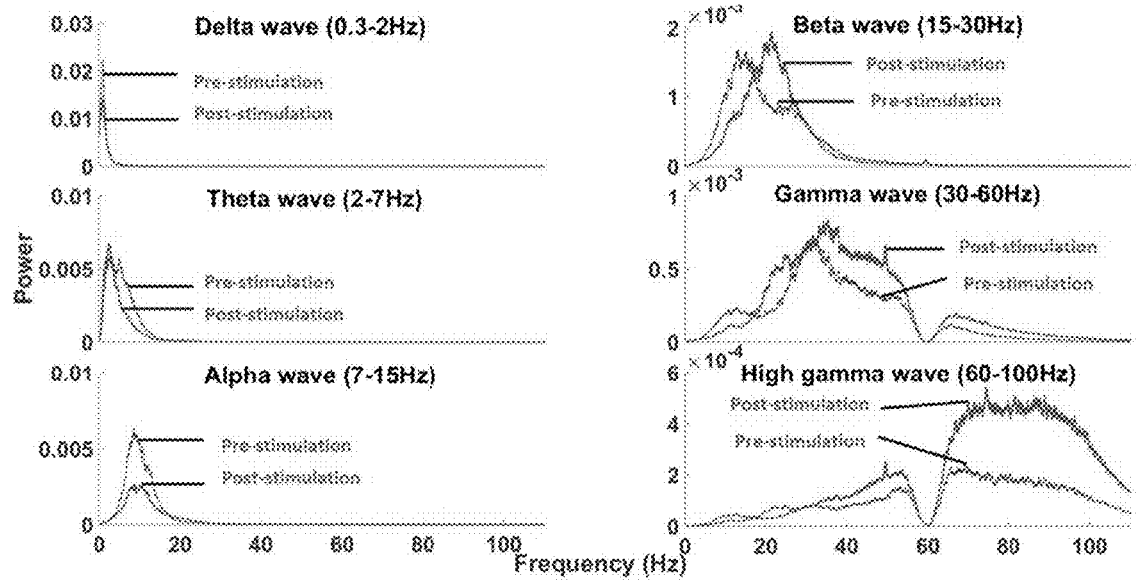
Figure 12:
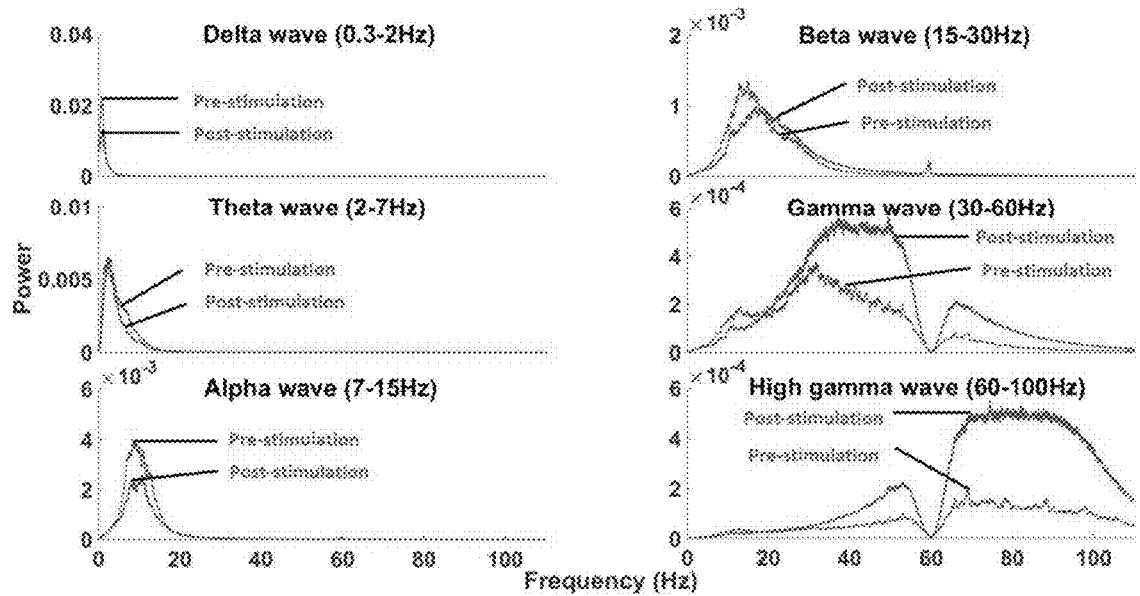

Referring now to FIG. 12, the LFP from pre-stimulation and post-stimulation session are compared together as shown. Unlike the previous comparison, the whole session of LFPs was compared before and after the 1000 seconds stimulation session. FIG. 12($a$) through ($d$) represent signals recorded from 4 different channels (electrodes). By calculating frequency band power dissipation, an increase in power spectrum after stimulation session in high frequency oscillations (beta, gamma and high gamma) has been observed. Specifically, 15 Hz to 20 Hz is the cutoff frequency point where energy below this cutoff frequency does not increase, but energy higher than the cutoff frequency has apparently increase significantly. Since high frequency oscillations are related to motion movement, the stimulation applied during the experiment worked as a reinforcement for hand motion as evidenced by an increase in the energy spectrum in high oscillation bands associated with sensorimotor motion.

The system described herein offers a small form factor while providing similar or better functional capabilities than offered by other works in one single 30 mm PCB design. The system integrates functions including neural signal recording, neural stimulator, wireless data and power transfer that avoid excessive surgeries for implantable devices. The number of channels (32) for recording and (4) stimulation is useful for most clinical applications and exceeds those reported in the literature. The power consumption is low and a novel wireless power transfer technique is integrated to the system. Communication between devices and host is completely wireless by using a proprietary protocol offering up to 2 Mbits/sec.

Example—Brain and Remote System

Figure 13:
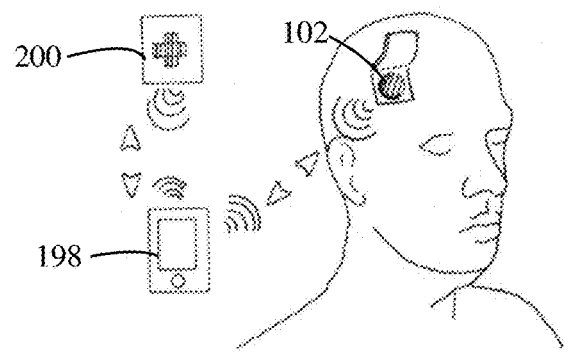
FIG. 13 is a line drawing showing a model of the human head having an implantable device in wireless communication with a local handheld device, and the local handheld device in wireless communication with a remote medical facility, node, or server.

Referring now to the figures, FIG. 13 is a line drawing showing a model of the human head having an implantable device 102 in wireless communication with a local handheld device 198, and the local handheld device 198 in wireless communication with a remote medical facility, node, or server 200. In this non-limiting example, a pair of BBMI implanted devices 102 are used to wirelessly communicate with a remote device 198. Raw brain-generated electrically detectable signals are received by a brain implanted electrode attached to an implanted bidirectional brain machine interface container as described herein, where the signals are wirelessly transmitted to an external handheld or computer 198, which may or may not be further networked. Raw brain signals are converted/sampled to digital signals using an A-to-D converter in the container, where the digital signals are optionally further processed, e.g. LNA amplified, filtered, channel coded, modulated, encrypted, and/or HPA amplified for transmission, before the digital signals are transmitted to the external device 198, 200 for recording, and analysis. The remote device 198 then transmits a return signal to the implanted BBMI device 102, where the signal provides instructions to perform further recording, provide electronic stimuli through the same electrode 130 as the recording area, or to a different electrode/array 202 than the electrode from the recording area, to update or reset the BBMI device, or to adjust the BBMI device settings.

Figure 14:
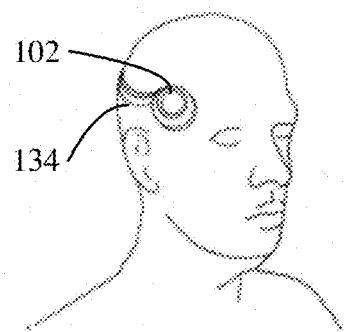
FIG. 14 is a line drawing showing a model of the human head having a device implanted at or below the temporal bone area with wires trailing posteriorly towards the occipital part of the skull

FIG. 14 is a line drawing showing a model of the human head having a device 102 implanted at or below the temporal bone area with wires trailing posteriorly towards the occipital part of the skull. The wire(s) 134 can be used to increase antenna size and thereby signal gain, or the additional wires 134 can lead to a secondary BBMI device 102 implanted in the rear of the skull (not shown).

Example—Wired Brain and Torso System

Figure 15:
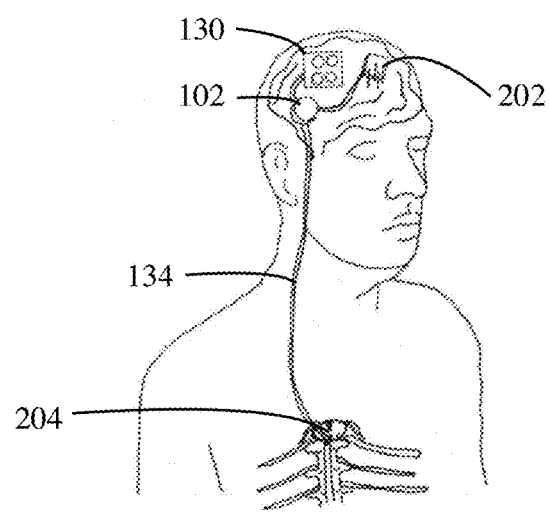
FIG. 15 is a line drawing showing a model of the human head and torso having an implanted device located at or below the temporal bone area with wire leads connecting to a sensor array or electronic treatment device within the brain with a second descending wire leading to the descending lumbar area or the sternum area of the torso.

FIG. 15 is a line drawing showing a model of the human head and torso having an implanted device 102 located at or below the temporal bone area with wire leads 134 connecting to a sensor array 130 or electronic treatment device 202 within the brain with a second descending wire 134 leading to the descending lumbar area or the sternum area of the torso. In this non-limiting example, a BBMI brain implanted device 102 is used to communicate (transmit and receive) with a remote torso-implanted device 204. In one direction, raw brain-generated electrically detectable signals are received by a brain implanted electrode/array attached to a first implanted bidirectional brain machine interface container as described herein. The signals are transmitted by wire implant 134 to a second remote torso-implanted BBMI device 204. The captured raw brain signals are converted/sampled to digital signals using an A-to-D converter in the first container, where the digital signals are optionally further processed, e.g. LNA amplified, filtered, channel coded, modulated, encrypted, and/or HPA amplified for transmission, before the digital signals are transmitted to the remote device for generating and delivering electronic stimuli. The remote device 204 also transmits return signals, e.g. recording of remote effect, to the first implanted BBMI device 102, where the return signal provides instructions to perform recording/analysis in the brain region, provide brain electronic stimuli through the brain electrode 130, or to record or provide stimuli to a different electrode/array 202 than the electrode from the recording area, or also to update or reset the BBMI device(s), or to adjust the BBMI device settings.

Example—Wired Multi-BBMI Device System

Figure 16:
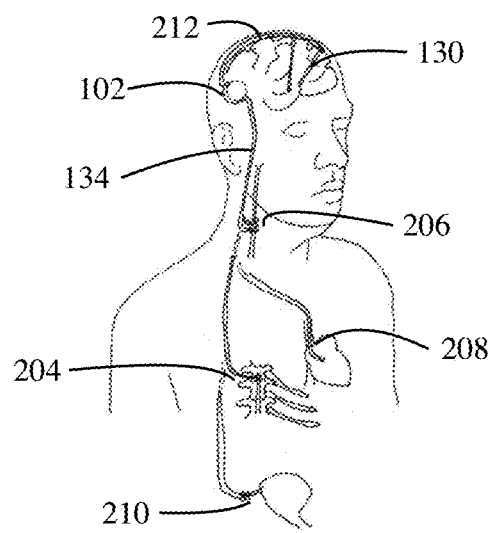
FIG. 16 is a line drawing showing a model of the human head and torso having an implanted device located at or below the temporal bone area with wire leads connecting to a sensor array or electronic treatment device within the brain with a series of descending wires leading to vascular anatomy of the neck, leading to the heart, descending lumbar area or the sternum area of the torso, and descending to the peritoneal space to interface with an organ.

FIG. 16 is a line drawing showing a model of the human head and torso having an implanted device 102 located at or below the temporal bone area with wire leads 212 connecting to a sensor array 130 or electronic treatment device within the brain with a series of descending wires 134 leading to vascular anatomy of the neck, leading to the heart, descending lumbar area or the sternum area of the torso, and descending to the peritoneal space to interface with an organ. In this non-limiting example, there is a (first) Brain implanted BBMI device 102, a brain implanted electrode/array 130 connected to the Brain BBMI 102. A second electrode/array 206 in the neck that is connected by wire 134 to the Brain BBMI 102. A second Heart BBMI device 208 is implanted near the heart having appropriate cardiac electrode(s) and connected by wire 134 in a circuit with the Brain BBMI device 102. A third Spinal BBMI device 204 implanted near, on, or within the spine having appropriate electrode(s) for transmitting and receiving stimuli and recorded signals to and from the spinal cord nerves or related nerve roots, ganglia, neurons, or axons, and which is connected by wire 134 in a circuit with the other BBMI devices 102, 208, 210. And a fourth Organ BBMI device 210 implanted near, on, or within a organ having appropriate electrode(s) for transmitting and receiving stimuli and recorded signals to and from the organ, e.g. bladder, kidney, pancreas, islet cells, stomach, small intestine, large intestine, rectum, liver, spleen, gall bladder, or other peritoneal tissue, etc.

Example—BBMI Device Structure

Figure 17:
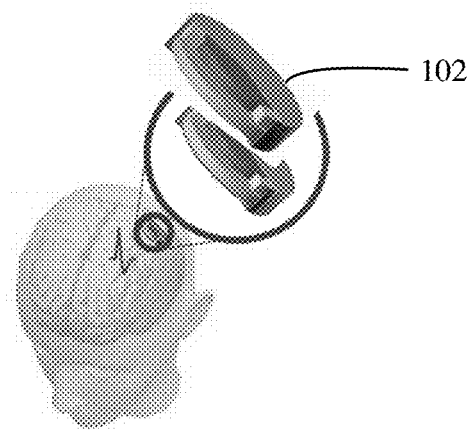
FIG. 17 is a graphic showing the device having a case and internal components shown for size comparison against the human head.
Figure 18:
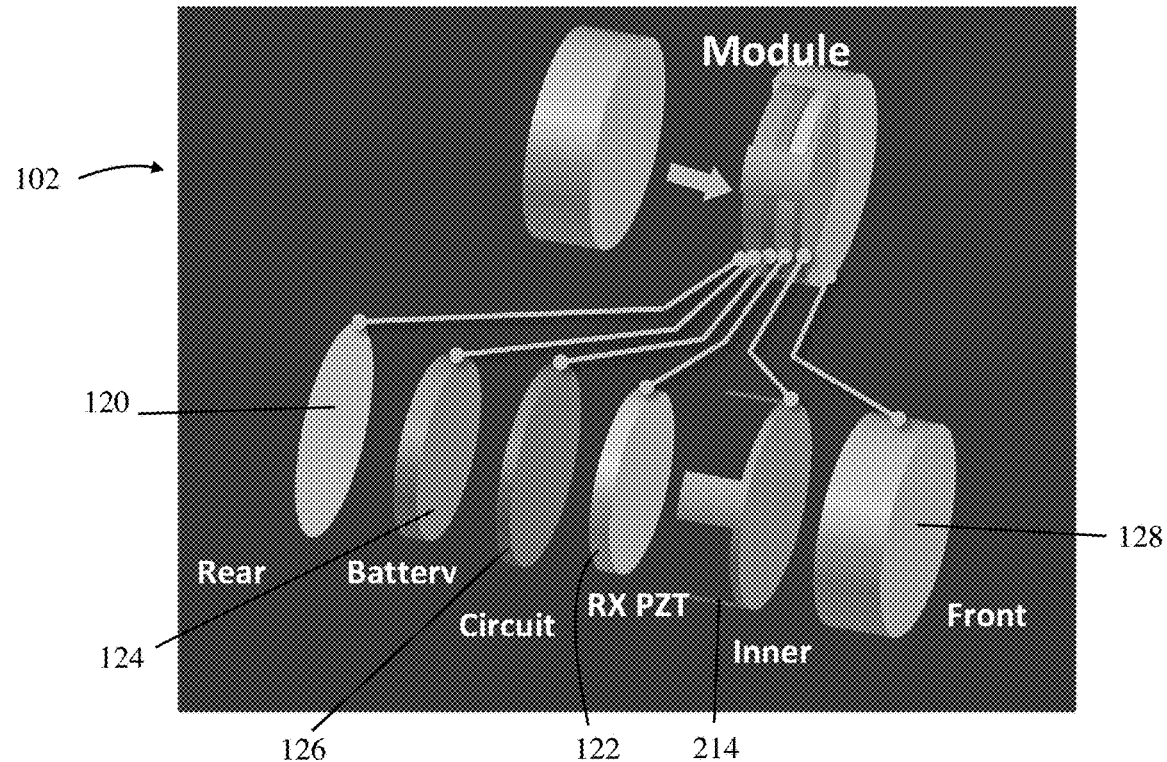
FIG. 18 is a graphic showing one example of the overall component diagram of the device, including within the exterior case a stacked series of components in an interior area comprised of a battery component, a circuit component, a transceiver, and an optional inner frame.

Referring now to FIGS. 17-23, the invention has the components for the bi-directional neural-communication device integrated with the wireless power transfer module with a rechargeable battery to provide the required power source for the circuits (FIGS. 17 and 18). FIG. 17 shows a graphic showing the device 102 having a case and internal components shown for size comparison against the human head. FIG. 18 shows a graphic showing one example of the overall component diagram of the device 102, including within the exterior case 120, 128 a stacked series of components in an interior area comprised of a battery component 124, a circuit component with a transceiver 126, power receiver 122, and an optional inner frame 214.

Example—Patient Monitoring

In another preferred embodiment, the technical characteristics of the bi-directional neural-communication device are summarized as follows. The device can both record from an electrical signals sensor and stimulate target tissue or nerve that provides a closed loop bidirectional interface solution while recording from the neural tissue also provides components for stimulation. The on-board computing will monitor the patient's condition and calculate the right parameters to induce stimulation to the target area based on the sensor data. The sensor reading circuit can be connected to the existing implantable sensors such as for neural, glucose, oxygen, cardio, bladder, muscle motion sensors, etc. with minimal interfacing. The on-board computation circuit controls complex bidirectional input/output processes and wireless communication with external device. The on-board computation circuit takes periodic or continuous measurements of sensor signals, conducts real time sensor-data analysis to detect abnormal conditions and automatically correct the stimulation setting and ensures timely delivery of parameter to the stimulation circuit. Access to the wireless data can be secured and authenticated.

A good technical quality of a neural implant is to be as small as possible in order to be to minimally invasive, particularly in areas surrounding the brain. One of the technical features of this invention is providing a new of method of placing a neural implant in the skull—becoming a part of skull structure, and not adding any volume increase/size increase to a patient's head. However, by making a small-size implantable BBMI, it is essential to provide a power supply unit with a rechargeable battery.

Example—Mobile Solution

In another example, neurostimulation is managed by mobile phone. The BBMI implant(s) can be configured to communicate with user's external cell phone (wirelessly). This provides a closed-loop solution monitoring real time sensor data collected from the patient as the stimulation parameter is autonomously adjusted based on the status of the patient. When used as a smart neurostimulator for pain control, this provides patients with control and monitoring of their progress relating to pain or pain-related disorders. It can also monitor the state of a patient during and after a stimulation session, and replace or augment damaged senses. As stated, the device provides two-way communication between the human neural information and physical stimulation devices. When the device is used in a mobile terminal setting (i.e., a smart-phone), the mobile network tools can be used for a secure and safe connected active monitoring/control system. Providing timely sensor data will enable the terminal to wirelessly monitor patients' status closely and take corrective stimulation actions autonomously. The invention also addresses a security and authenticity issue that does not exhibit itself in stand-alone neuroprosthetic implants.

Since the device is designed to include a security and authentication problem that presents itself in connected systems, the invention, provides an end-to-end patient-doctor connectivity solution via mobile network by securely acquiring sensor readings from the patient's neural signals from the nerve, and securely manage and control the active stimulation signal.

Example—Ultrasound Charging Integrated BBMI

Power is received through wireless power transmission to the implant, e.g. through the skin. The tissue surrounding the implant is usually highly sensitive to temperature rise, meaning that power consumption must be minimal in order to prevent tissue damage. The invention is configured to provide minimal temperature increases. Several prototypes have been developed that incorporate this feature of the invention.

In one embodiment, an ultrasonic wireless power transmission system was fabricated—i.e. receiver/transmitter to provide the required electric power as part of the closed-loop, co-adaptive, bi-directional brain-machine interface (BBMI) system.

The ultrasonic power transmission system has two novel piezoelectric transducers, facing each other between skin tissues converting electrical energy to mechanical vibrational energy or vice versa. Since ultrasound is free from the electromagnetic coupling effect and does not interfere with medical frequency bands, ultrasound is excellent for implantable purposes. In this invention, a novel piezoelectric composite transducer, rectifier circuit, and rechargeable battery have been developed, all packaged in biocompatible titanium container. Experimental results demonstrate that the prototype device can reach 50% of energy transmission efficiency in a water medium at 20 mm distance and 18% in animal skin tissue at 18 mm distance, respectively.

Figure 19:
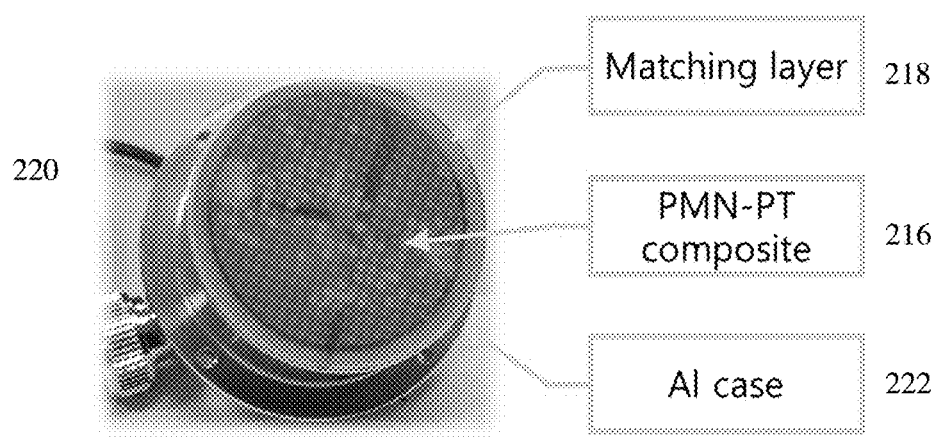
FIG. 19 is a photograph of one embodiment of that shows the prototype components for the proposed ultrasonic power transfer system including a. Novel piezoelectric composite; b. a. Receiver unit; c. Coin-Type rechargeable battery; d. Power-Management circuit), packaged into a Ti-case.

FIG. 19 shows the prototype components for the ultrasonic power transfer system that were manufactured from our on-going project effort, and include: a. Novel piezoelectric composite 216; b. Transmitter/transducer unit 218; c. Power-Management circuit 220; d. case 222.

Figure 20:
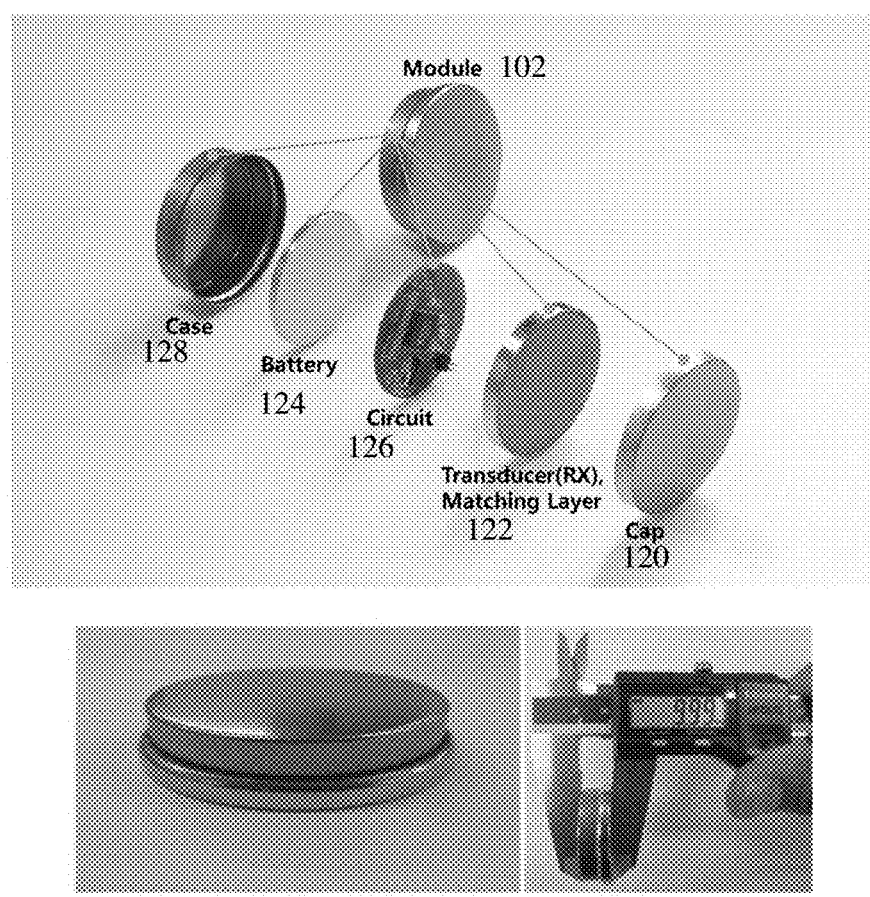
FIG. 20 is a series of three photographs showing one embodiment of a prototype device having a. Novel piezoelectric composite; b. a. Receiver unit; c. Coin-Type rechargeable battery; d. Power-Management circuit.

FIG. 20: The prototype BBMI device 102 as manufactured, including lower case 128, and upper case cap 120, with battery 124, circuit/SoC 126, and power receiver/transducer 122 packaged neatly inside. Calipers show thickness in one non-limiting embodiment to be approx. 9.99 mm.

Example—MIMO and 16×16 Processing

Another aspect of the invention is a multi-channel input/output interface circuit utilizing low-power Bluetooth for near field wireless communication. In this non-limiting example, the invention provides hardware and software for a wireless spinal stimulator system with 16 channels of recording and four channels of stimulation that is integrated with ultrasonic charging control circuits. The ultrasonic wireless charging and wireless monitoring capability includes integrated firmware and software, and provides 20-25% charging efficiency steadily. The BBMI includes a wireless stimulator, manufactured and tested as, a 3.5-cm diameter employing a 16 channel Intan chip for an analog front end. The BBMI includes a control circuit for the 16-channel stimulation circuitry and wireless communication protocol is implemented using a system on a chip from a Nordic Semiconductor. For communication of the neural recording, the BBMI implements a lightweight protocol based on enhanced shock burst (ESB) protocol. The BBMI can optionally be configured with Bluetooth Low Energy communication protocol. The ESB protocol has a bandwidth of 1.5 Mbits/sec minimum data rate. The stimulation/pulse circuit delivers single as well as bi-phase pulses. The circuitry implements a multiplexing of the stimulation and recording electrodes. The container uses a Ti biocompatible packaging for efficient simultaneous power charging as well as wireless data transmission.

In one embodiment, the signal is routed through a network. In another embodiment, the signal is routed to a user feedback screen. Raw and processed signals from the acquisition device, and the device command, can be communicated via a local area network to one or more computers. As with other electronic devices, the signal may be further passed through a low pass-filter, amplifiers, oscillators, modulation devices, encoding devices, and A-to/from-D converters.

Figure 21:
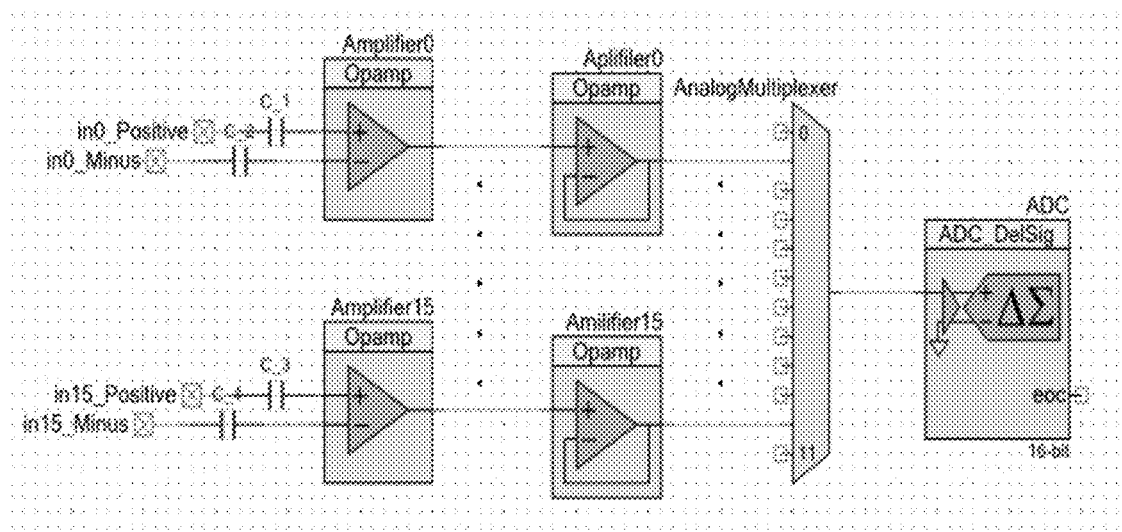
FIG. 21 is a prototype multichannel interface circuit diagram.
Figure 22:
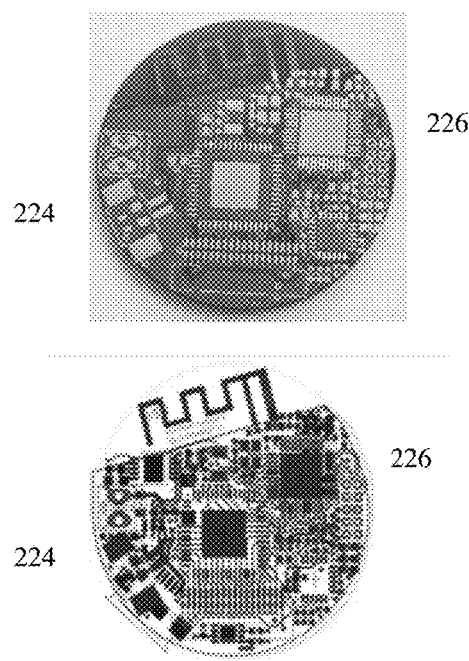
FIG. 22 is a photograph of a circuit board and an illumination of the circuits of a prototype 16 Channel BCI interface circuit with low-power multi-channel wireless data transmission circuit.
Figure 23:
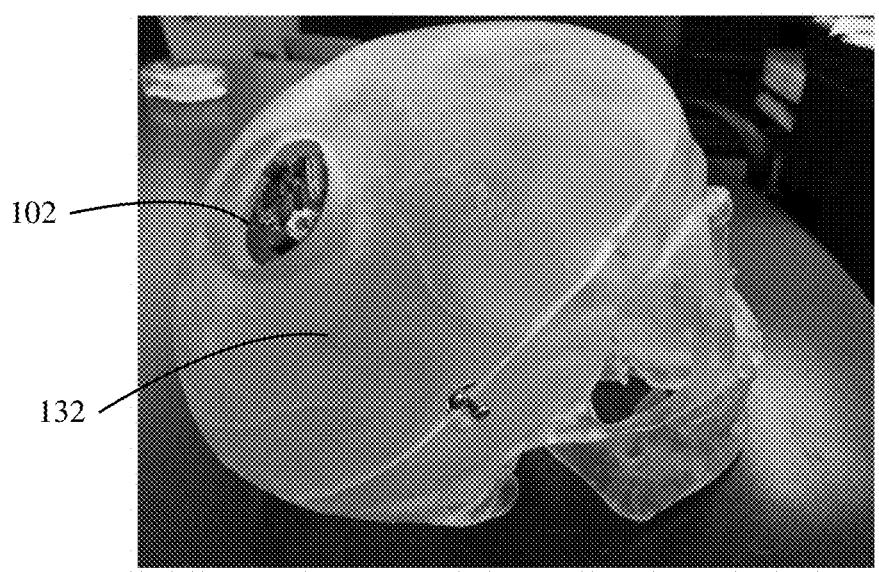
FIG. 23 is a photograph of a plastic model of a human skull having a prototype 16 Channel BCI interface circuit with low-power multi-channel wireless data transmission circuit embedded within the skull material near a parietal bone area of the model.

The prototype has a low-power bidirectional interface that can record 16 channels of neural tissue activity and generate 16 channels of stimulation. An on-board microprocessor is used to control real time stimulation parameters such as frequency, duty-cycle, amplitude, etc. using periodic or continuous measurements of sensor signals. The portion of the bidirectional interface circuit is shown in FIGS. 21, 22 and 23. FIG. 21 shows a prototype multi-channel interface circuit diagram. FIG. 22 shows prototype 16 Channel BCI interface circuit with low-power multi-channel wireless data transmission circuit. FIG. 23 shows a prototype BBMI device implanted in a skull model with BBMI unit having a 16 Channel BCI interface circuit with low-power multi-channel wireless data transmission circuit.

Example—Wireless Spinal Stimulator

Figure 24:
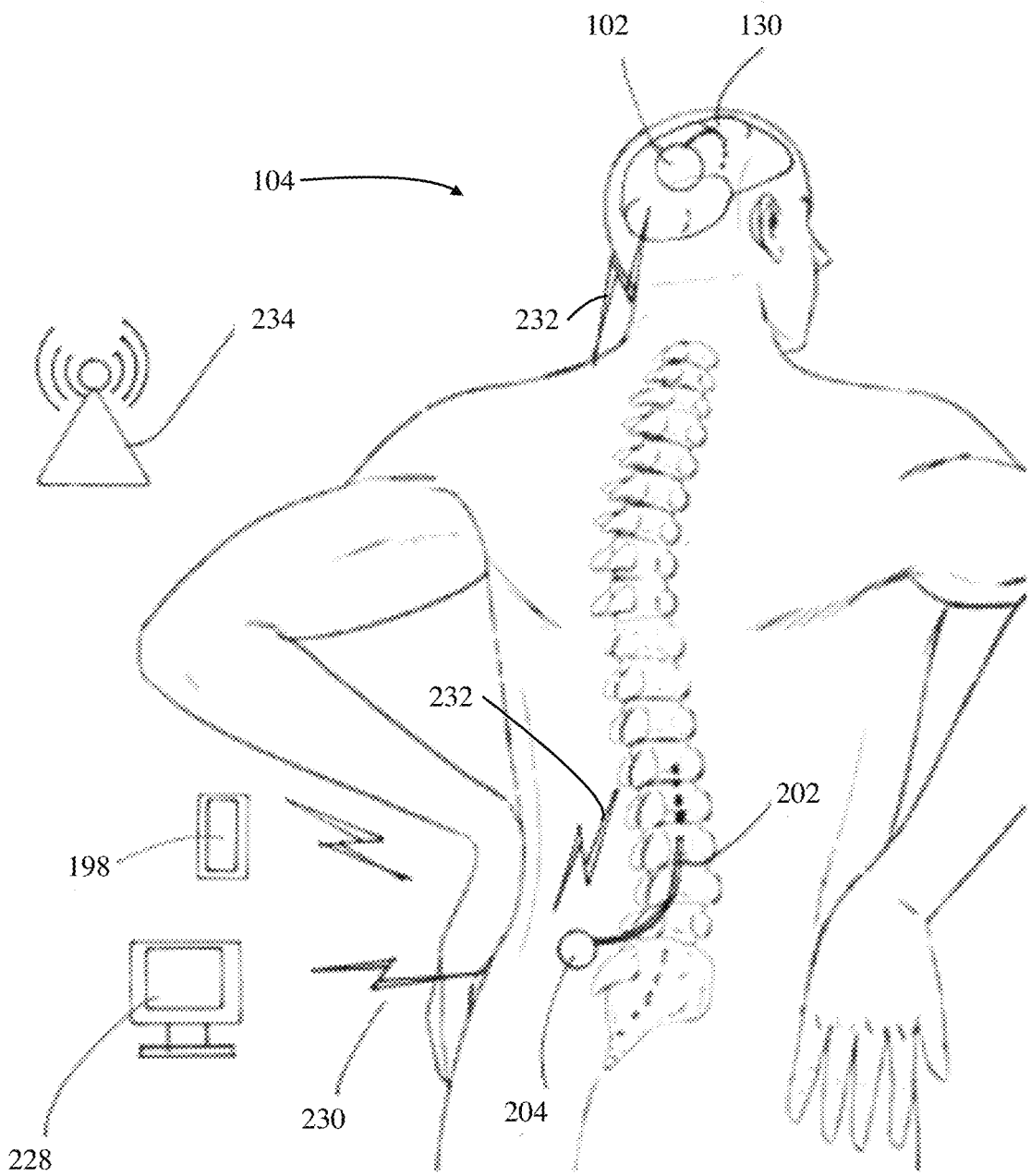
FIG. 24 is a graphic sketch and shows: (1) wireless spinal stimulator; (2) spinal electrodes; (3) brain-computer interface (BCI); (4) BCI electrodes; (5) external controller; (6) smart phone controller; (7) wireless network.

Referring now to FIG. 24, is a system configuration of one embodiment of the invention and shows a non-limiting example of an implantable wireless spinal stimulator system 104.

Similar to the cranially deployed container 102, the container deployed for spinal uses 204 is a small and low power wireless spinal stimulator. It provides a wireless connection 230 between a head-fixed BBMI 102 with electrodes 130, or to an external remote controller 198, 228. System 104 can be used alone as a Spinal BBMI 204, or in conjunction with a brain implanted BBMI 102. It is a fully implanted spinal stimulator that is recharged via ultrasound 234. The invention addresses problems that may be produced by wire connections that can be broken and become infected. This prototype offers 16 stimulation channels as well as 16 reading channels. In this example, the stimulation output 202 is triggered wirelessly from the BBMI 204 or the external controller 198, 228 to the spinal BBMI 204 or the external controller 198, 228 to the cranial BBMI 102, then to the spinal BBMI 204.

As stated, the invention is a neural communication device providing the spinal stimulation and recording function. The invention can be can be connected using existing networking technologies such as Bluetooth or ESB (Enhanced Shock-Burst) for wireless data communication. The invention has an integrated ultrasonic power transfer through the skin for wirelessly charging an implanted secondary rechargeable battery. It provides several advantages over the conventional wireless recharging technologies including the small form-factor, low-temperature effect, deep power transmission distance, etc. The implantable bi-directional neural-communication device uses a custom portable recharging system using the ultrasonic power transmission that was developed by the investigators.

Figure 25:
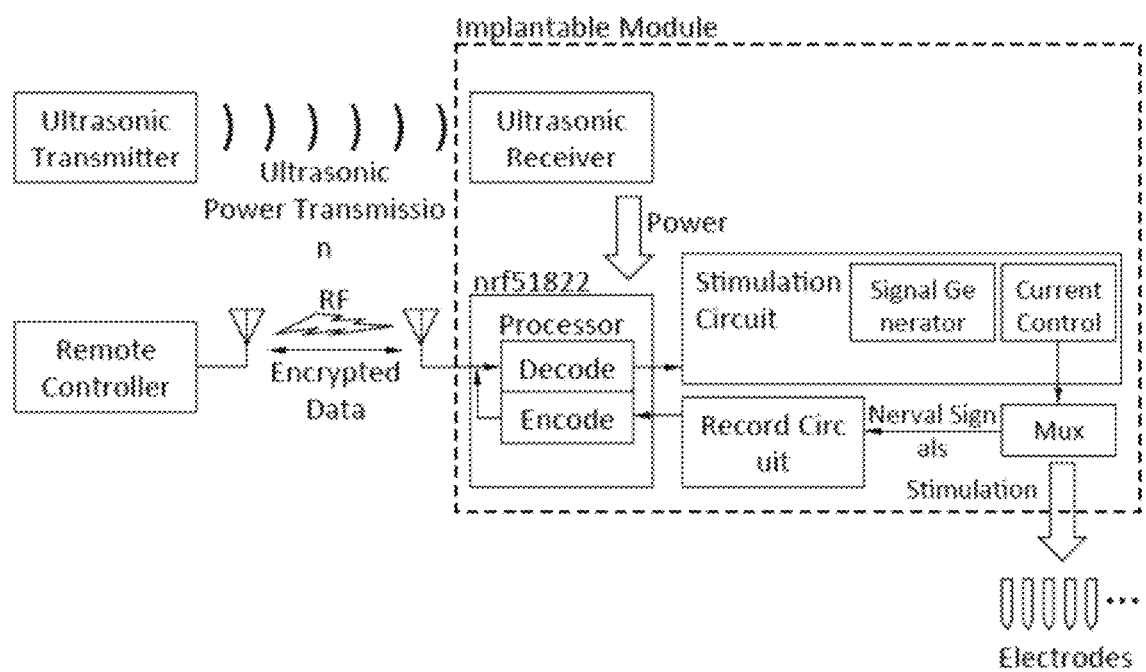
FIG. 25 is an architectural overview and shows a wireless spinal stimulator functional block diagram.

FIG. 25 shows the system diagram of the spine stimulator. FIG. 25 shows ultrasonic transmitter in wireless connection with ultrasonic receiver. Ultrasonic receiver provides power to the communication, stimulation, and recording components. Remote controller is shown sending and receiving wireless signals to and from the wireless capabale processor. Processor contains encoder and other circuitry necessary for connecting to stimulation circuit and recording circuit. Stimulation circuit include a signal generator and a current control module, which is connected through a multiplexer to the electrode array for providing the electronic stimuli. Recording circuit receives neural signals from the multiplexer connected to the electrode array or a second electrode array.

Table 1 shows the functional capability of the invention.

TABLE 1

Specifications of two implantable spinal stimulators

Number of stimulating channels: 16
Number of recording channels: 16
Output characteristics: Adjustable voltage (+−18 V)
Waveform type: Bipolar-phase
Pulse frequency: 0-250 Hz
Pulse width: 100-300 µs
Power dissipation: 25 mW Example—Treatment In this non-limiting example, a patient presents with a condition, diagnosis, complaint, or issue generally recognized as a medical disorder, process, disease, condition, or pathology. Contemplated as within the scope of the invention are disorders, processes, diseases, conditions and pathologies selected from: chronic leg or arm pain, failed back surgery syndrome, complex regional pain syndrome, arachnoiditis, stump pain, angina, peripheral vascular disease, multiple sclerosis, spinal cord injury, stroke, non-stroke ischemic event, paralysis, brain injury, neurological pain, neurological injury of any kind, quadriplegic, paraplegic, traumatic brain injury, damage caused by cancer or arising from cancer treatment such as chemotherapy or radiation therapy nerves disorders, genetic or hereditary diseases, disorders or syndromes, epilepsy, neuralgia, tremor, Parkinson's, seizures, neurological tics, cervical or lumbar spinal disc or nerve disorders, neuropathic pain, sympathetically mediated chronic pain, motor command disorders, speech pathologies, sleep apnea, hearing or visual disorders, memory disorders, cognitive disorders, and psychiatric disorders and disease recognized in DSM IV. Treatment using the BBMI device herein is performed, and results in reducing, eliminating, or ameliorating one or more signs or symptoms, temporarily or more permanently, during the treatment process or upon completion of the treatment, of one or more of the above listed disorders, processes, diseases, conditions, or pathologies. "Treatment" may also include reduction of pain, allowing a patient to resume daily activities, reduction of pain medication, improved relaxation, physical therapy including therapy to improve strength, use, coordination, tone, blood supply and nerve conduction in and/or improved sleep.

Example—Native Enhancement

In this non-limiting example, a patient requests medical intervention to enhance native processing of hearing, vision, speech, motor control, and other types of neuronal perception. Treatment using the BBMI device herein is performed, and results in improvement of the native capabilities of the patient.

Figure 26:
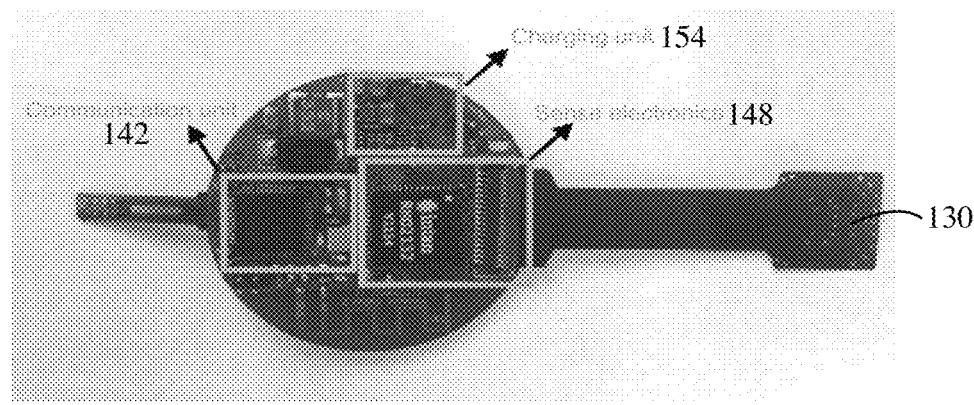
FIG. 26*a-b-c* is a series of three photos showing device size and component views.
Figure 26:
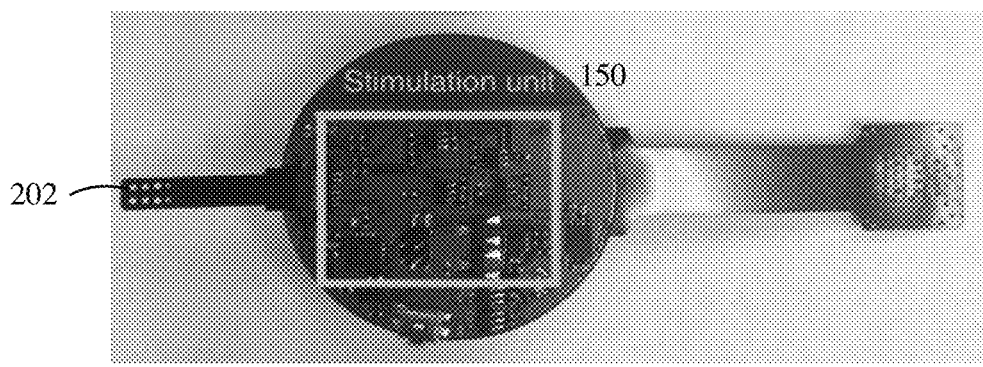
Figure 26:

Referring now to FIG. 26a-b-c, FIG. 26 illustrates in a series of three photos the device size and component views. Communication unit chip 142 is connected to charging unit circuit 154, and sensor electronics module 148. Sensor electrodes 130 and stimuli electrodes 202 are shown attached to the circuitry. FIG. 26b shows stimuli module 150.

FIG. 27*a-b-c* Recording from the first prototype of the device. (a) applied stimulation to the cortex and recorded stimulation artifacts. (b) brain data wirelessly recorded from the implantable device.

Figure 27:
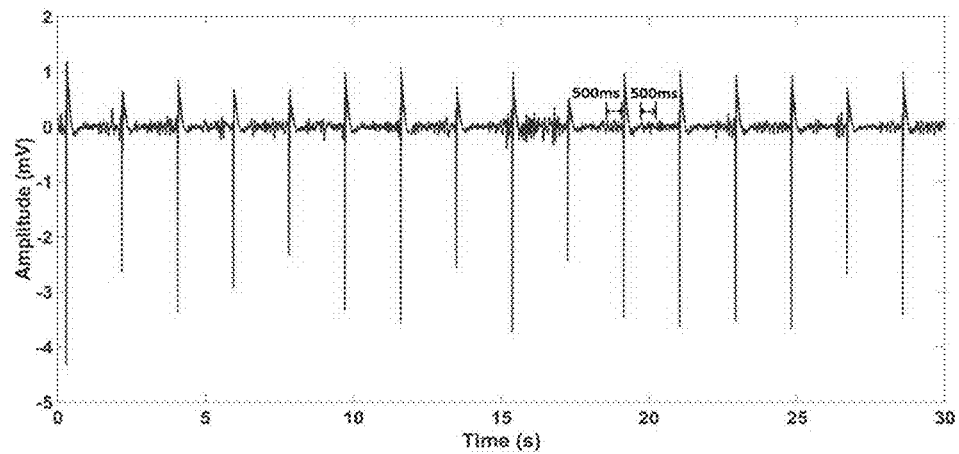
FIG. 27*a-b-c* Recording from the first prototype of the device. (a) applied stimulation to the cortex and recorded stimulation artifacts. (b) brain data wirelessly recorded from the implantable device. (c) wirelessly controlled implantable stimulator for the wireless corticospinal BBMI system block diagram.
Figure 27:
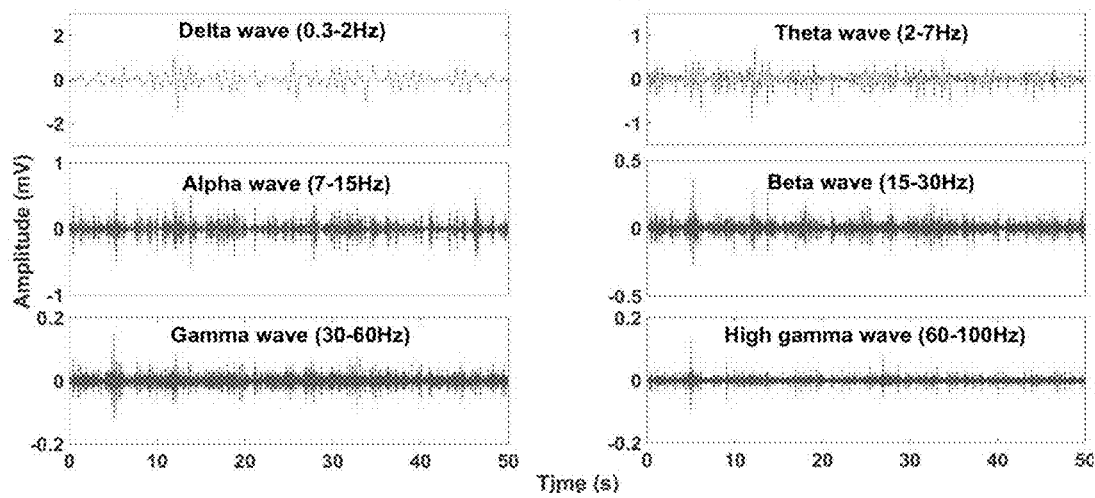
Figure 27:
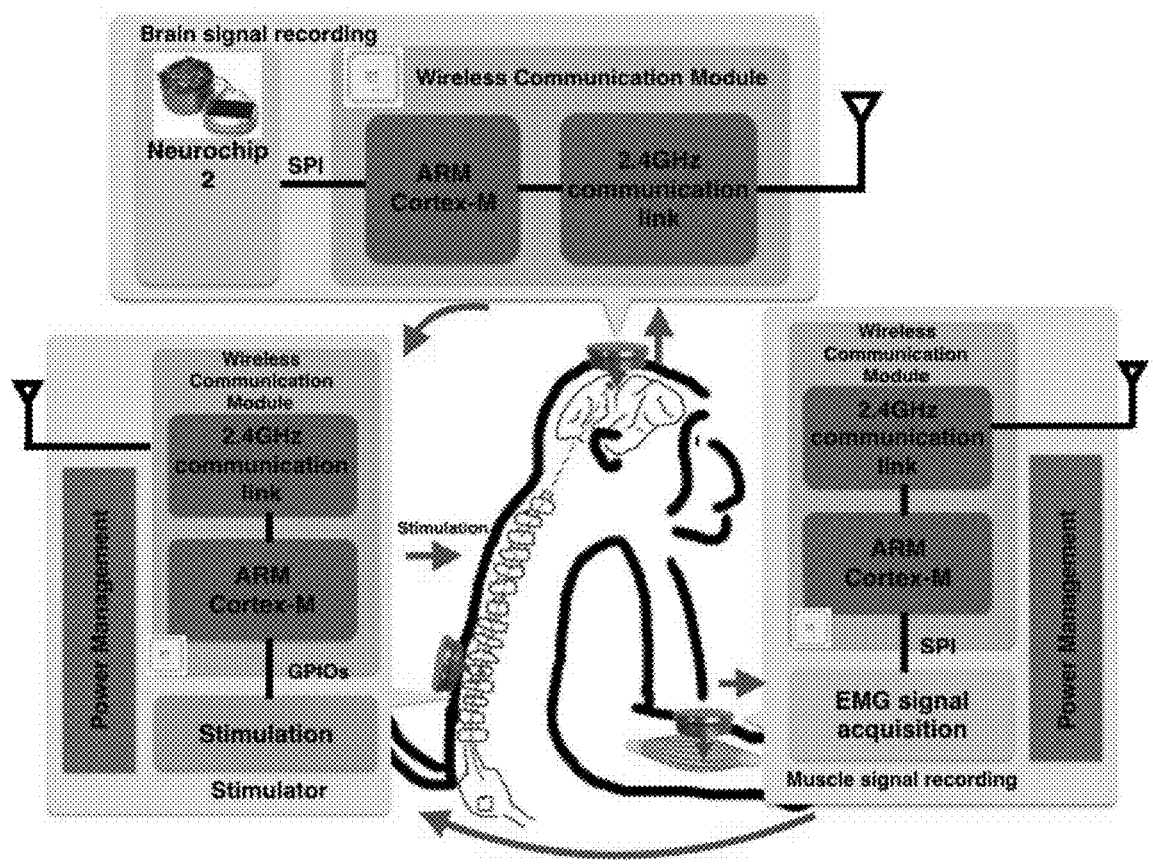

FIG. 27(*c*) shows a multi-device system of wirelessly controlled implantable stimulators for the wireless corticospinal BBMI system block diagram. FIG. 27*c* shows Brain BBMI 102 in wireless connection to spinal BBMI 204, and both or either is also in wireless communication with forearm implant BBMI 236.

FIG. 28 is chart showing details of the number of channels, and signal characteristics.

Example—Spinal Treatment

Neuroplasticity is an intrinsic property of the human central nervous system (CNS) and represents the ability of actively adapting to environmental pressures, physiological changes, and experiences. Systems that can interpret brain activity and use it to control prosthetic devices or promote rehabilitation of sensorimotor system have immense potential. A small, low power wireless implantable spinal stimulator is proposed to connect the skull implant device to the stimulating electrodes in the spinal cord of primates allowing neural activity in motor cortex to control spinal stimulation. The invention provides a new spine-implantable bi-directional spinal stimulation device combining recording and the stimulation functions into a small form factor neurostimulation device.

A bi-directional neural-communication and spinal stimulation device is developed. The bi-directional neural-communication device have the capability of both recording and stimulating the target neurons providing a closed loop solution. In addition the spinal stimulation device is integrated to the skull implant device.

The spine stimulator is able to deliver 16 channels of stimulation to the spinal electrode array. It can be recharged using an ultrasound transducer, eliminating all infection-prone transcutaneous leads. A bi-direction communication module connects the spinal stimulation unit with the skull implant device.

The communication link between the skull implant device and the stimulator is based on a proprietary micro Enhanced ShockBurst (μESB) protocol based on 2.4 GHz communication link.

The system also implements an implantable wireless EMG module planned as a fore-arm implant in order to achieve targeted, activity-dependent spinal stimulation (TADSS). To achieve TADSS, the intraspinal micro-stimulation below the injury point will be synchronized with the arrival of functionally related volitional motor commands signaled by electromyographic activity (EMG) in the impaired limb. TADSS will be delivered in conjunction with retraining of a forelimb behavior to augment use-dependent physical therapy. Stimulator will be controlled by skull implant device and implanted EMG to generate triggers for intraspinal stimulation.

One of the key challenges of wireless bio-signal transmission is the limited communication bandwidth between transmitter and receiver. The proprietary μESB protocol can support up to 2 Mbits/sec bandwidth. This provides the capability for a broad range of different target physiological signal recording.

A small form factor, low power wireless implantable spinal stimulator was developed. A wireless EMG module is integrated to the skull implant device via a wireless communication module added to the skull implant device. The spinal prototype offers 16 stimulation channels and the output can be triggered wirelessly by the skull implant device in spike triggered stimulation and by the implanted EMG module for TADSS.

Example—2π Piezo

Figure 29:
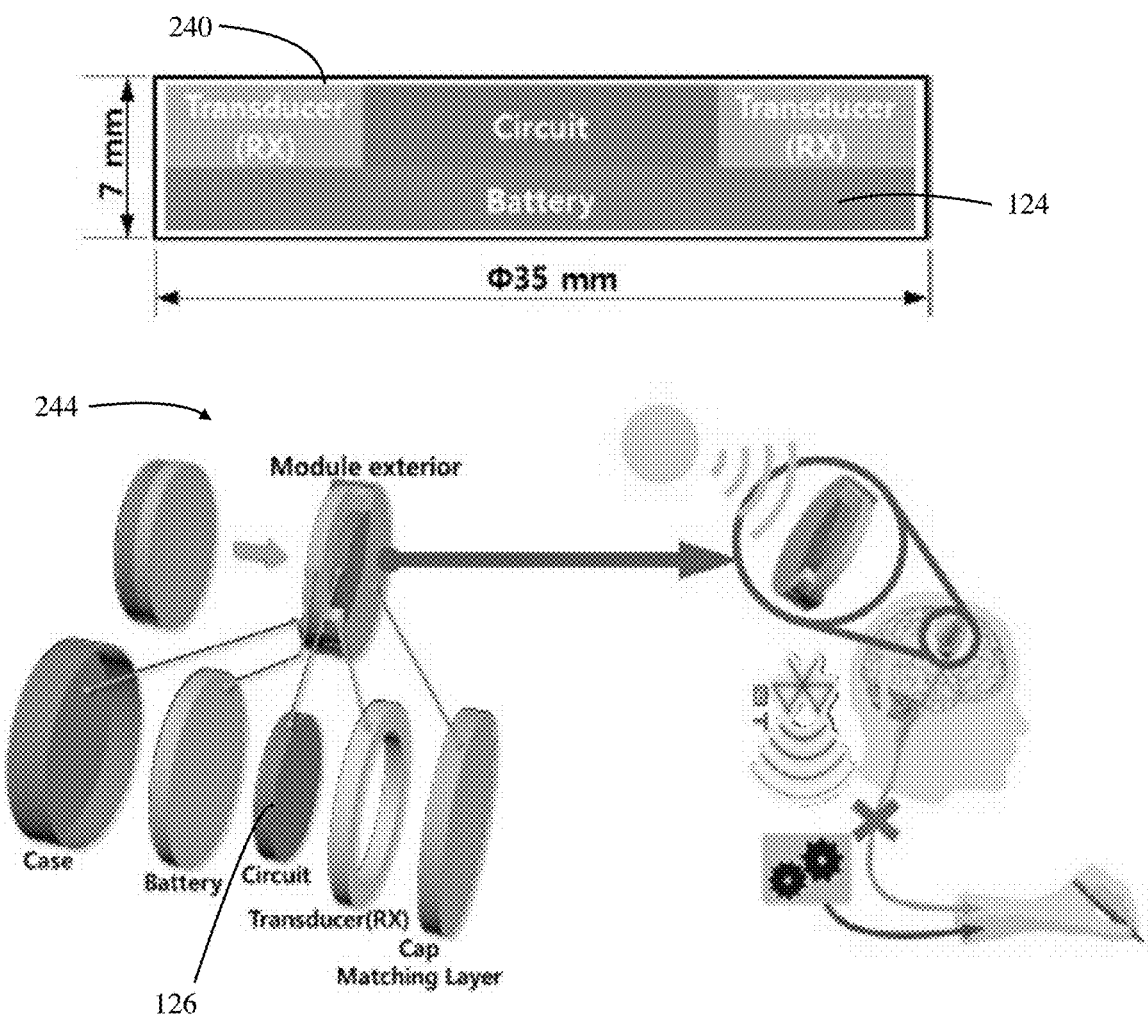
FIG. 29 is an illustration showing Component Diagram of the Closed-loop, Co-adaptive Bi-directional Brain-Machine Interface (BBMI) Engineered System in an exploded view of a cut-away detail view, and a plan (side) view of one embodiment of a BBMI device.

Referring now to FIG. 29, a transducer circumferentially encompasses the circuitry 126, e.g. SoC, sensor module, stim module, power control module. This "2π" piezo ultrasonic wireless power transmission system is shown as part of the closed-loop, co-adaptive, bi-directional brain-machine interface (BBMI) system 244 to provide the required electric power.

Figure 30:
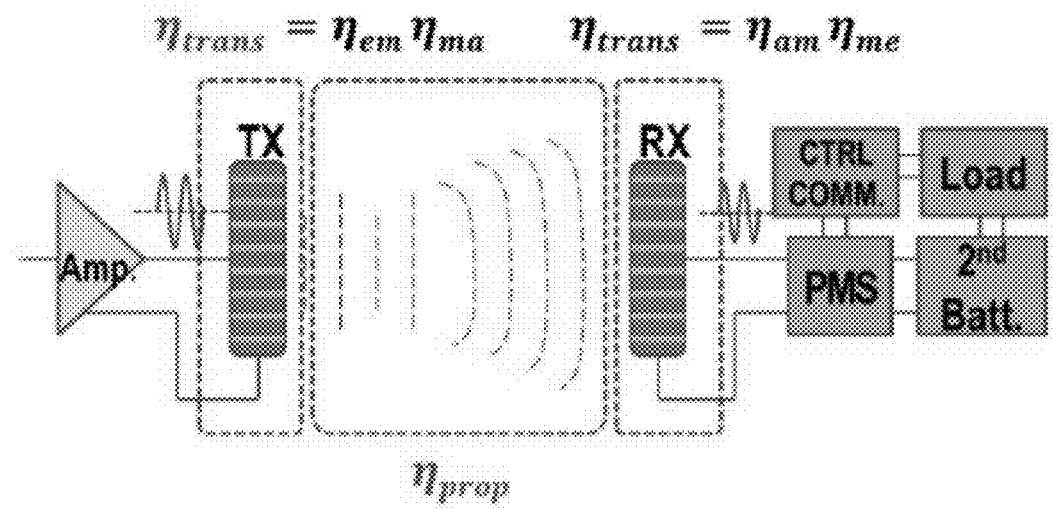
FIG. 30 is an illustration of Ultrasonic wireless power transfer system is composed of transmitting transducer, medium, receiving transducer, power management system and 2nd battery.

In this example, the ultrasonic power transmission system has a novel piezoelectric transducer 240 facing each other between skin tissues converting electrical energy to mechanical vibrational energy or vice versa. This wireless power transfer module has a rechargeable battery 124 to provide the required power source for the BBMI Engineered System 244. As previous described, the ultrasonic wireless power transfer system converts electrical energy to ultrasonic energy. Then, a receiver that converts the ultrasonic energy to the electrical energy again. This allows the generated acoustic wave to travel through the media, such as tissue, wirelessly. (FIG. 29, FIG. 30).

Figure 31:
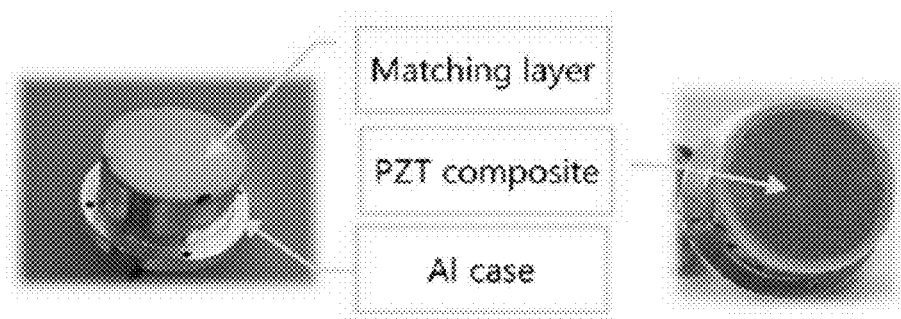
FIG. 31 is a set of photos showing the manufactured ultrasonic transducer with matching layer.

FIG. 31 shows a matching layer and an AI case with the PZT composite between them. The ultrasonic resonance transmitter and receiver are the same size of 30.0 mm diameter, 3.0 mm height. It has a matching layer of ¼λ of driving frequency. The piezoelectric material is PZT 5H. It is a type of 1-3 composite. (FIG. 31).

Figure 32:
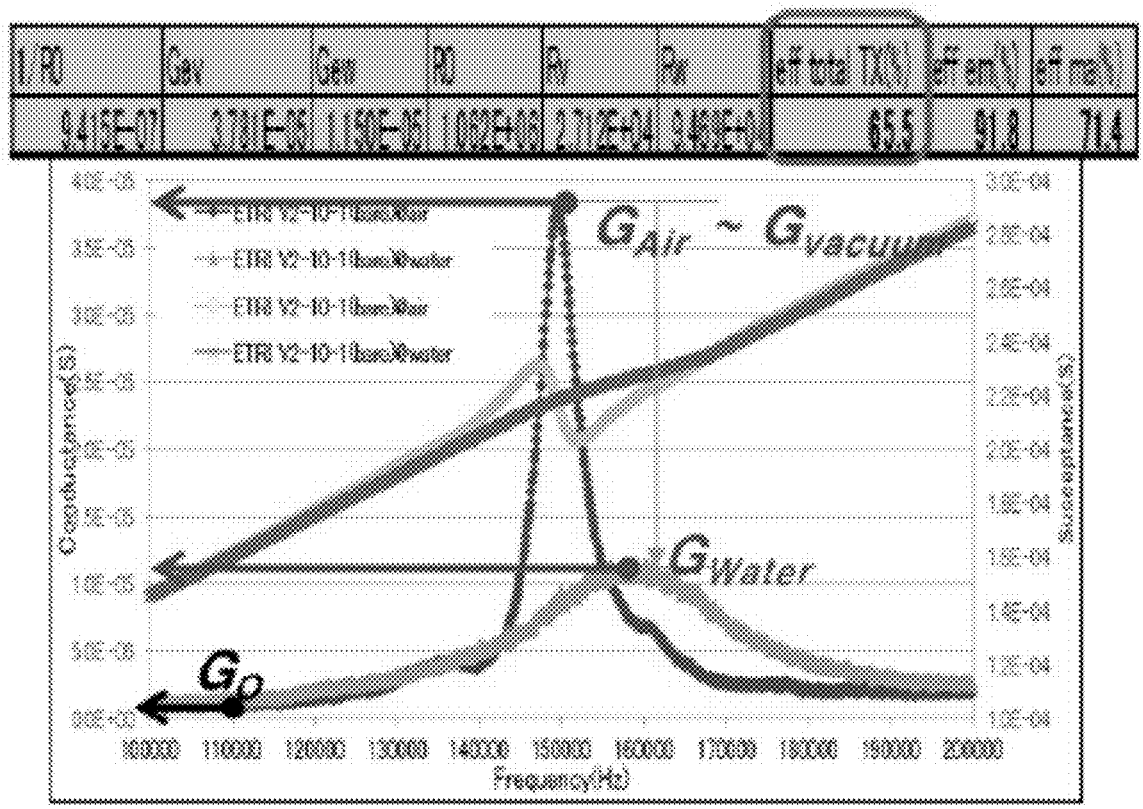
FIG. 32 is a graph showing the coupling efficiency of the transducer to the (water) medium.

Referring now to FIG. 32, impedance is measured using HP 4194A. The results are shown. FIG. 32, shows a red dot line representing measured results in the air. The green cross line represents the measured data in water (media). The total coupling efficiency was calculated to be 65.5%. The efficiency from electric to mechanical energy conversion is almost 92%. The efficiency from mechanical to acoustic energy conversion is 71.5%. There can be some a conversion loss from mechanical to acoustic energy due to imperfection of matching layer.

Figure 33:
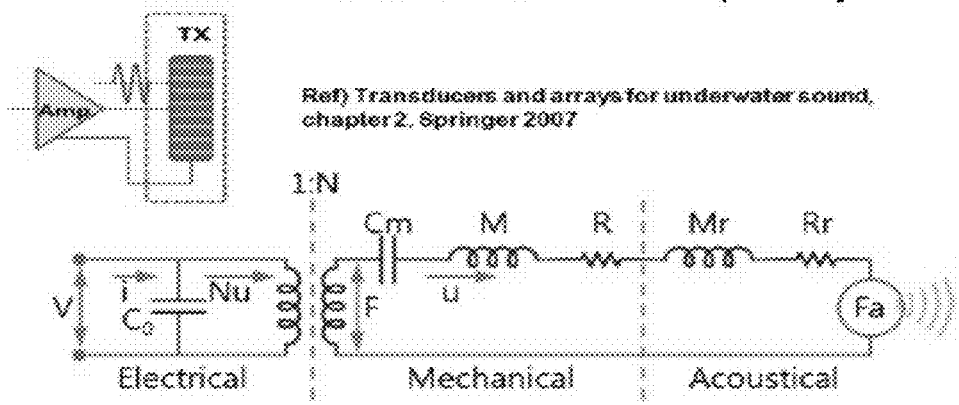
FIG. 33 is an illustration showing the equations governing the admittance and impedance related to the function of the transducer.

Referring now to FIG. 33, the equations governing the relationship between admittance, and impedance are provided. Where, Gm, G0 is the admittance, R is impedance of transducer. Rair, Rw, R0 is the impedance of air, water and dc level, respectively.

Figure 34:
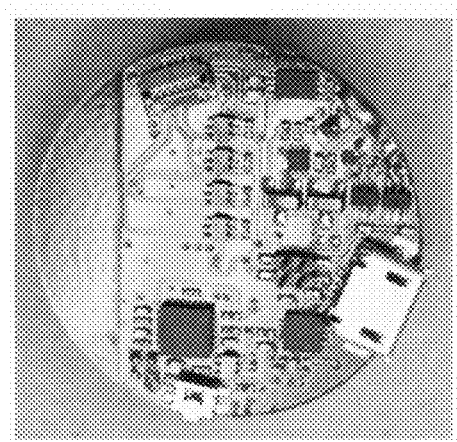
FIG. 34 is a photo of printed circuit board (PCB) schematic of a wireless power transfer system using ultrasonic resonance.

FIG. 34 shows the schematic of the wireless power transmission system using ultra-sonic resonance principle.

Figure 35:
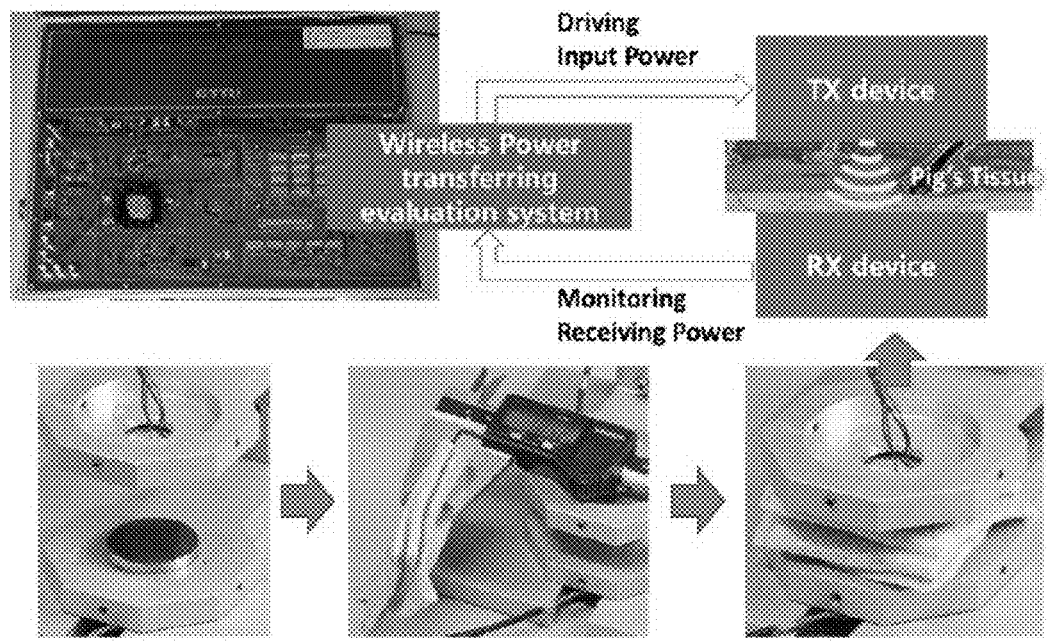
FIG. 35 is a set of photos showing a wireless power transfer evaluation system using porcine tissue to simulate human skin over an implant BBMI.

FIG. 35 illustrates the wireless power transfer evaluation system. The transmit device (tx) and the receive device (rx) are separated by porcine tissue as a proxy for human skin.

Figure 36:
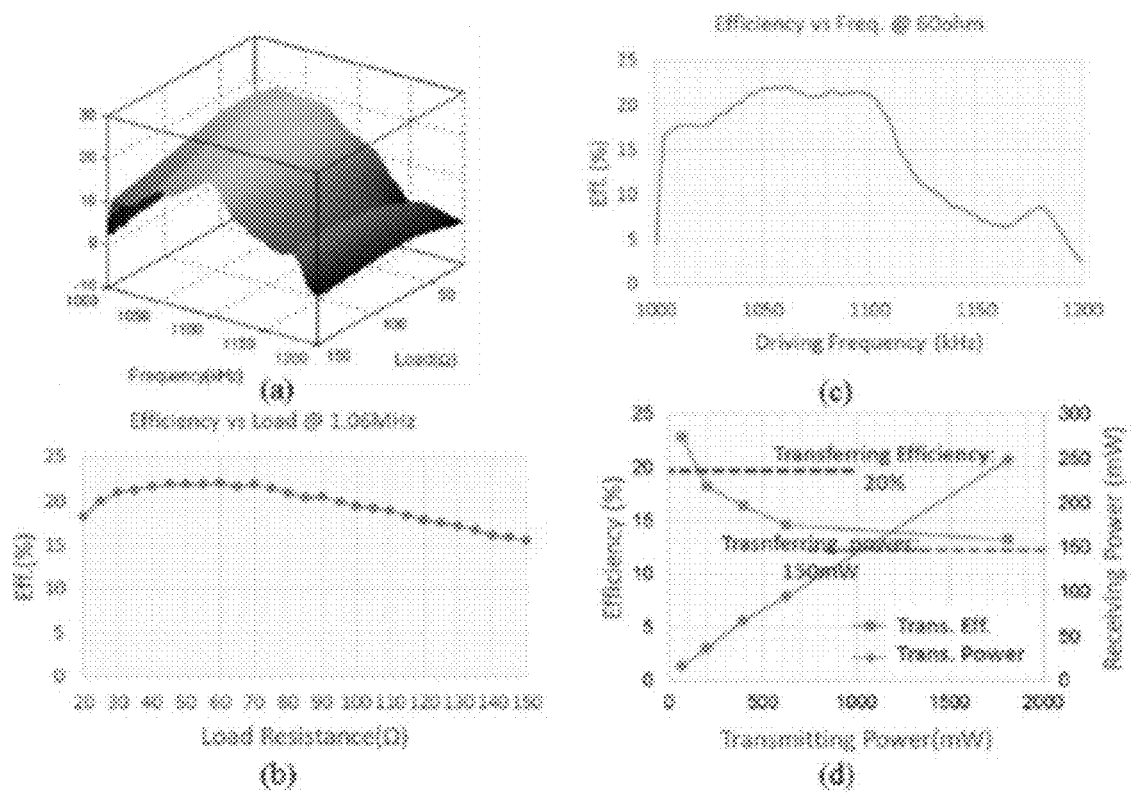
FIG. 36 is a series of 4 graphs showing experimental results of the wireless power transfer evaluation system.

As shown in FIG. 36, the wireless power transferring efficiency is the ratio between receiving power to input power. The receiving power is the function of driving frequency and load. The Maximum wireless power efficiency is at the load 60 ohms when the internal resistance of RX is similar to load resistance (FIG. 36(*b*)). The maximum wireless power efficiency is at the driving frequency of 1.05 MHz (FIG. 36(*c*)). The maximum efficiency is 22.6% (FIG. 36(*d*)).

Considering the practical limit of input power (~1 W), the maximum transferring power would be 150 mW. The piezoelectric transducer, a rectifier circuit, and a rechargeable battery are all packaged in a biocompatible titanium housing, which is free from electromagnetic interference. The integrated prototype device has a diameter of 35 mm and the thickness of 10 mm.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

The invention claimed is:

1. A bi-directional brain-machine interface (BBMI) device, comprising:
   a biocompatible container housing an ultrasonic wireless power module, said power module comprises a piezoelectric composite transducer connected to a power rectifier circuit, and a rechargeable battery, wherein the piezoelectric composite transducer forms an internal part of a wireless two-part ultrasonic power transmission system having an external piezoelectric composite transducer paired with the internal part for wirelessly transferring power to recharge the rechargeable battery;
   a wireless RF communication System on Chip (SoC) within the housing, said SoC having a processor core and powered by the power module, said processor core configured to control wireless data transmission and reception, said processor core configured to control charging of the rechargeable battery, said processor core configured to acquire sensor output data, said processor core configured to control stimulation input pulses, and said SoC configured to use low-power near field wireless communication;
   a sensor electronics module that interfaces with the SoC and comprises a digital electro-physiology interface chip, a programmable amplifier, and analog to digital converter, wherein the sensor electronics module is configured to record at least 16 channels of neural tissue activity;
   a stimulation module that interfaces with the SoC and comprises a pulse circuit configured to transmit electrical stimuli, wherein the pulse circuit is configured to generate at least 4 channels of stimulation; and,
   a bidirectional microelectrode array that interfaces with the sensor electronics module and the stimulation module, wherein the bidirectional microelectrode array is configured to provide a bidirectional interface to record neural tissue activity and transmit electrical stimuli.

2. The BBMI device of claim 1, further comprising at least one spinal electrode connected to the stimulation module for transmitting electrical stimulation to the spine.

3. The BBMI device of claim 1, wherein the biocompatible container is a circular disc having a diameter ranging from 25-100mm, and a height ranging from 8-30 mm.

4. The BBMI device of claim 1, wherein the biocompatible container is a circular disc having a diameter ranging from 28-75mm, and a height ranging from 10-20 mm.

5. The BBMI device of claim 1, wherein the biocompatible container is a circular disc having a diameter ranging from 30-50mm, and a height ranging from 10-20 mm.

6. The BBMI device of claim 1, wherein the biocompatible container is a circular disc having a diameter less than or equal to 35mm, and a height less than or equal to 10 mm.

7. The BBMI device of claim 1, wherein the biocompatible container is comprised of one or more a materials selected from the group consisting of a metal, a polymer, or a composite.

8. The BBMI device of claim 1, wherein the biocompatible container is comprised of one or more a materials selected from the group consisting of titanium, Nitinol(R), surgical steel, calcium, copper, zinc, iron, cobalt, magnesium, manganese, vanadium, molybdenum, silicate, strontium, tungsten, chromium, nickel, aluminum, and ceramics, composites, alloys, compounds, and mixtures thereof.

9. The BBMI device of claim 1, wherein the biocompatible container is comprised of one or more a materials selected from the group consisting of polyurethane (PU), polyesters, polyethers (PEEK), silicones, silicates, poly(vinyl chloride) (PVC), acrylates, methacylates, dextran, synthetic rubber (cis-polyisoprene), polyvinyl acetate, Bakelite, polychloroprene (neoprene), nylon, polystyrene, polyethylene, polypropylene, polyacrylonitrile, polyvinyl butyral (PVB), poly(vinylidene chloride), fluorinated polymers, polytetrafluoroethylene (PTFE), and mixtures and copolymers thereof.

10. The BBMI device of claim 1, wherein the biocompatible container comprises a biocompatible coating selected from calcium phosphate, tricalcium phosphate, or hydroxyapatite.

11. The BBMI device of claim 1, wherein the rechargeable battery is a Lithium ion battery.

12. The BBMI device of claim 1, wherein the processor core is configured to turn off module components that are not active to conserve battery.

13. The BBMI device of claim 1, wherein the low power near-field wireless communication comprises a 2.4 GHz protocol.

14. The BBMI device of claim 1, wherein the low power near-field wireless communication has a data rate ranging from 250 Kbps-2 Mbps.

15. The BBMI device of claim 1, wherein the low power near-field wireless communication comprises a Bluetooth Low Energy (BLE) communication protocol or an Enhanced ShockBurst (ESB) protocol.

16. The BBMI device of claim 1, wherein the low power near-field wireless communication has a transmit power ranging from 0.01-2.5 mW (−20 dBm to 4 dBm).

17. The BBMI device of claim 1, wherein the low power near-field wireless communication has a minimum data rate bandwidth of 1.5 Mbits/sec.

18. The BBMI device of claim 1, wherein the analog to digital converter is 16-bit.

19. The BBMI device of claim 1, wherein the sensor electronics module includes a built-in temperature sensor, and wherein the SoC is configured to monitor tissue temperature and implement device changes to avoid tissue damage from high temperatures.

20. The BBMI device of claim 1, wherein the sensor electronics module is configured to record at least 32 channels of neural tissue activity.

21. The BBMI device of claim 1, wherein the pulse circuit is configured to generate at least 16 channels of stimulation.

22. The BBMI device of claim 1, wherein the pulse circuit is configured to generate at least 32 channels of stimulation.

23. The BBMI device of claim 1, wherein the pulse circuit is configured to generate bi-phase pulses.

24. The BBMI device of claim 1, wherein the sensor electronics module is configured to record at least 32 channels of neural tissue activity and wherein the pulse circuit is configured to generate at least 32 channels of stimulation.

25. The BBMI device of claim 1, wherein the SoC is configured to monitor at least 32 channels of recorded neural tissue activity and wherein SoC is configured to direct the pulse circuit to generate stimulation to a pre-programmed channel of stimulation based on recorded neural tissue activity.

26. The BBMI device of claim 1, wherein the SoC is configured to implement multiplexing of signals for stimulation and signals for recording.

27. The BBMI device of claim 1, wherein the SoC is configured to perform simultaneous power charging and wireless data transmission.

28. The BBMI device of claim 1, further comprising a memory device connected to the SoC.

29. The BBMI device of claim 1, further comprising a remote computer in wireless communication with the SoC.

30. An integrated bi-directional neural-communication and spinal stimulation system, comprising at least two of the BBMI devices of claim 1, wherein the BBMI devices are configured to communicate and operate in a closed-loop, wherein a first BBMI device is configured to transmit a signal to a second BBMI device that is configured to receive the signal, and wherein the first BBMI device is configured to generate the signal when the SoC of the first BBMI device records neural tissue activity, and wherein the second BBMI device is configured to direct electrical stimuli when the SoC of the second BBMI receives the signal.

31. The integrated bi-directional neural-communication and spinal stimulation system of claim 30, comprises three of the BBMI devices of claim 1, wherein the BBMI devices are configured to communicate and operate in a closed-loop, wherein the BBMI devices are configured to transmit and receive signals to and from each other, wherein a first BBMI device is configured to generate the signal when the SoC of the first BBMI device records neural tissue activity, and wherein the second BBMI device is configured to direct spinal electrical stimuli when the SoC of the second BBMI receives the signal, and wherein the third BBMI device is configured to generate a second signal when the SoC of the third BBMI device records peripheral neural tissue activity, and wherein the first BBMI device is configured to direct electrical stimuli when the SoC of the first BBMI receives the second signal.

32. A method of transmitting a signal from a brain to a computer, comprising the steps:
implanting the device of claim 1 into the skull of a patient with the sensor array and the electrode in operative communication with the brain of the patient; and,
transmitting a signal from the device to an external receiver.

33. A method of treating a patient in need thereof, comprising the steps of:
implanting the device of claim 1 in the skull of a patient in need thereof;
transmitting and receiving signals to and from the device to treat a disease or disorder selected from the group consisting of: epilepsy, motor command pathologies including paralysis, speech disorders, sleep apnea, pain, neurological tics, multiple sclerosis, neurological disorders, hearing or visual disorders, memory disorders, psychiatric disorders including depression, and cognitive disorders.

34. A method of treating a patient in need thereof, comprising the steps of:
implanting the device of claim 1 in the skull of a patient in need thereof; and,
transmitting and receiving signals to and from the device to enhance native processing of hearing, vision, speech, motor control, and other types of neuronal perception or control.

35. an implantable wireless spinal stimulator, comprising:
a biocompatible titanium container housing a piezoelectric composite transducer connected to a power rectifier circuit, and a rechargeable battery, wherein the piezoelectric composite transducer forms an internal part of a two part ultrasonic power transmission system having an external piezoelectric composite transducer paired with the internal part for transferring power to recharge the rechargeable battery;
an RF module having a wireless transceiver, a circuit board, an antenna device, and a processor interface, said RF module connected to the rectifier circuit;
said RF module comprising a multi-channel input/output bidirectional interface circuit connected to the wireless transceiver, said interface circuit configured to use low-power Bluetooth for near field wireless communication, wherein the interface circuit is configured to record 16 channels of neural tissue activity and the interface circuit is configured to generate 16 channels of stimulation;\
a microprocessor connected to the RF module, said microprocessor is used to control real time stimulation parameters such as frequency, duty-cycle, amplitude, etc. using periodic or continuous measurements of sensor signals, said microprocessor recording, controlling, and processing signal reception and transmission, said microprocessor connected to a memory device;
at least one spinal electrode connected to the RF module for transmitting electrical stimulation to the spine; and
a sensor array connected to a brain-computer interface (BCI) on the microprocessor for receiving electric signals from the brain.

36. A method of transmitting an electrical stimulus from a brain to a computer to a spine, comprising the steps:
implanting the device of claim 2 or 35 into a lumbar area of a patient with the spinal electrode in communication with spinal nerve(s) and the sensor array in operative communication with the brain of the patient; and,
transmitting a stimulus from the computer to the spine based on a signal from the brain to the computer.

37. A method of treating a patient in need thereof, comprising the steps of:
implanting the device of claim 2 or 35 in the lumbar area of a patient in need thereof;
transmitting and receiving signals to and from the device to treat a spinal disease or disorder.

38. A method of treating a patient in need thereof, comprising the steps of:
implanting the device of claim 2 or 35 in the lumbar area of a patient in need thereof; and,
transmitting and receiving signals to and from the device to enhance native processing of spinal nerve activity or control.

* * * * *

UNITED STATES PATENT AND TRADEMARK OFFICE
CERTIFICATE OF CORRECTION

| | |
|---|---|
| PATENT NO. | : 10,452,143 B2 |
| APPLICATION NO. | : 15/295988 |
| DATED | : October 22, 2019 |
| INVENTOR(S) | : Moon et al. |

It is certified that error appears in the above-identified patent and that said Letters Patent is hereby corrected as shown below:

In the Specification

Column 1, Lines 20-23, Government Support Clause should read: "This invention was made with government support under grant number 1028725 awarded by the National Science Foundation. The government has certain rights in the invention.".

Signed and Sealed this
Fourteenth Day of May, 2024

Katherine Kelly Vidal
*Director of the United States Patent and Trademark Office*